United States Patent [19]

Hauptmann et al.

[11] Patent Number: 5,710,027
[45] Date of Patent: Jan. 20, 1998

[54] PROCESS AND VECTOR FOR EXPRESSING ALPHA-INTERFERON IN E. COLI

[75] Inventors: Rudolf Hauptmann, Ebreichsdorf; Edgar Falkner; Gerhard Bodo, both of Vienna; Tilman Voss, Mödling; Ingrid Maurer-Fogy, Vienna, all of Austria

[73] Assignee: Boehringer Ingelheim International GmbH, Ingelheim am Rhein, Germany

[21] Appl. No.: 249,671

[22] Filed: May 26, 1994

[30] Foreign Application Priority Data

May 26, 1993 [DE] Germany .......................... 43 17 459.0
Sep. 3, 1993 [DE] Germany .......................... 43 29 756.0

[51] Int. Cl.$^6$ .............................. C12N 15/70; C12N 15/21
[52] U.S. Cl. ................................... 435/69.51; 435/69.58; 435/320.1; 435/252.33; 530/412; 530/415; 530/416; 536/23.4; 536/23.52; 536/24.1
[58] Field of Search ..................... 435/69.51, 320.1, 435/252.33, 69.8; 530/412, 415, 416; 536/23.4, 23.52, 24.1

[56] References Cited

U.S. PATENT DOCUMENTS

| | | | |
|---|---|---|---|
| 4,769,327 | 9/1988 | Stephens et al. | 435/69.8 |
| 4,828,990 | 5/1989 | Higashi et al. | 435/69.51 |
| 4,917,887 | 4/1990 | Hauptmann et al. | 424/85.7 |
| 4,963,495 | 10/1990 | Chang et al. | 435/320.1 |
| 5,066,786 | 11/1991 | Protasi et al. | 530/351 |
| 5,196,323 | 3/1993 | Bodo et al. | 435/69.51 |
| 5,258,287 | 11/1993 | Baxter et al. | 435/69.1 |
| 5,367,060 | 11/1994 | Vandlen et al. | 530/399 |
| 5,455,165 | 10/1995 | Capon et al. | 435/69.7 |

FOREIGN PATENT DOCUMENTS

| | | |
|---|---|---|
| 0 115 613 | 8/1984 | European Pat. Off. . |
| WO 89/03225 | 4/1989 | WIPO . |

OTHER PUBLICATIONS

Voss, T. et al., "Periplasmic expression of human interferon-α2c in *Escherichia coli* results in a correctly folded molecule," *Biochem. J.* 298(3):719–725 (15 Mar. 1994).
Adolf, G.R., Monoclonal Antibodies and Enzyme Immunoassays Specific for Human Interferon(INF) ω1: Evidence that IFN-ω1 is a Component of Human Leukocyte IFN, *Virology* 175:410–417 (1990).
Beltz et al., Isolation of Multigene Families and Determination of Homologies by Filter Hybridization Methods, *Meth. Enzymol.* 100:266–285 (1983).
Bodo & Maurer–Fogy, Molecular Species of Recombinant Human Interferon Alpha 2 Detected in Affinity Purified Preparations. In: *The Biology of the Interferon System* (ed. Stewart, W.E., II Schellekens, H.), Elsevier Scientific Publishing Co., Amsterdam, pp. 59–64 (1985).
Breitling et al., Secretory expression in *Escherichia coli* and *Bacillus subtilis* of human interferon α genes directed by staphylokinase signals, *Mol. Gen. Genet.* 217:384–391 (1989).
Chang et al., Nucleotide sequence of the alkaline phosphatase gene of *Escherichia coli*, *Gene* 44:121–125 (1986).
Derwent World Patent Index, English language abstract of European Patent 0 115 613.
Dworkin–Rastl et al., Construction of expression plasmids producing high levels of human leukocyte–type interferon in *Escherichia coli*, *Gene* 21:237–248 (1983).
Fuh et al., The Human Growth Hormone Receptor, *J. Biol. Chem.* 265(6):3111–3115 (1990).
Goeddel et al., Human leukocyte interferon produced by *E. coli* is biologically active, *Nature* 287:411–416 (1980).
Goeddel et al., The structure of eight distinct cloned human leukocyte interferon cDNAs, *Nature* 290:20–26 (1981).
Hauptmann & Swetly, A novel class of human type I interferons, *Nucl. Acid Res.* 13(13):4739–4749 (1985).
Ho et al., Site–directed mutagenesis by overlap extension using the polymerase chain reaction, *Gene* 77:51–59 (1989).
Kafatos et al., Determination of nucleic acid sequence homologies and relative concentrations by a dot hybridization procedure, *Nucl. Acids Res.* 7(6):1541–1552 (1979).
Lee et al., Characterization of Gene Encoding Heat–Stable Toxin II and Preliminary Molecular Epidemiological Studies of Enterotoxigenic *Escherichia coli* Heat–Stable Toxin II Producers, *Infection and Immunity* 42(1):264–268 (1983).
Mantei et al., The nucleotide sequence of clones human leukocyte interferon cDNA, *Gene* 10:1–10 (1980).
Owen & Pitcher, Current Methods for Estimating DNA Base Composition and Levels of DNA–DNA Hybridization, *Chemical Methods in Bacterial Systematics*, pp. 67–93 (1985).
Picken et al., Nucleotide Sequence of the Gene for Heat–Stable Enterotoxin II of *Escherichia coli*, *Infection and Immunity* 42(1):269–275 (1983).
Shuttleworth et al., Sequence of the gene for alkaline phosphatase from *Escherichia coli* JM83, *Nucl. Acid Res.* 14(2):8689 (1986).
Streuli et al., At Least Three Human Type α Interferons: Structure of α2, *Science* 209:1343–1347 (1980).
Thatcher & Panayotatos, Purification of Recombinant Human IFN–α2, *Methods Enzymol.* 119:166–177 (1986).
Twigg and Sherratt, Trans–complementable copy–number mutants of plasmid ColE1, *Nature* 283:216–218 (1980).
Miyake, T., et al. (1985) *J. Biochem.* (Tokyo) 92: 1429–36.
Fuh, G., et al. (1990) *J. Biol. Chem.* 265: 3111–15.
Morioka–Fujimoto, K., et al. (1991) *J. Biol. Chem.* 266: 1728–32.

*Primary Examiner*—David L. Fitzgerald
*Attorney, Agent, or Firm*—Sterne, Kessler, Goldstein & Fox P.L.L.C.

[57] ABSTRACT

Methods and vectors for expressing interferon-alpha (IFN-α) proteins in *E. coli* are provided. Use of a vector comprising an IFN-α sequence fused to an *E. coli* heat-stable enterotoxin signal sequence (STII) under the control of the *E. coli* phosphatase (phoA) promoter affords high levels of correctly-folded and -processed, biologically active IFN-α polypeptides.

16 Claims, 7 Drawing Sheets

FIG. 1B

```
gaattggagattatcgtcactgcttcgcaatgtgccgcaaatgaccaac                        55
agcggttgattgatcagtgagggggcgctgcgaggtaaagcccgatgccag                      110
cattcctgacgacgatacggagctgcgcgcgattacgtaaagaagttattgaag                   165
catcctcgtcagtaaaagttaatctttcaacagctgtcataagttgtcacgg                     220
ccgagacttatagtcgctgttgttttaatgtatttgctcgagaggttg                         275
aggtgatttt ATG AAA AAG AAT ATC GCA TTT CTT GCA TCT                       318/11
           M   K   K   N   I   A   F   L   A   S
ATG TTC GTT TTT TCT ATT GCT ACA AAT GCC TAT GCA TGT GAT                  360/25
M   F   V   F   S   I   A   T   N   A   Y   A   C   D
CTT CCT CAG AAC CAT GGC CTA CTT AGC AGG AAC ACC TTG GTG                  402/39
L   P   Q   N   H   G   L   L   S   R   N   T   L   V
CTT CTG CAC CAA ATG AGA AGG AGA ATC TCC CCT TTC TGT CTC                  444/53
L   L   H   Q   M   R   R   R   I   S   P   F   C   L
AAG GAC AGA AGA GAC TTC AGG TTC CCC CAG GAG ATG GTA AAA                  486/67
K   D   R   R   D   F   R   F   P   Q   E   M   V   K
GGG AGC CAG TTG CAG GCC CAT GTC TCT GTC CTC CAT                          528/81
G   S   Q   L   Q   A   H   V   M   S   V   L   H
GAG ATG CTG CAG CAG ATC TTC AGC CTC TTC CAC ACA GAG CGC                  570/95
E   M   L   Q   Q   I   F   S   L   F   H   T   E   R
```

```
TCC TCT GCT GCC TGG AAC ATG ACC CTC CTA GAC CAA CTC CAC      612
 S   S   A   A   W   N   M   T   L   L   D   Q   L   H      109
ACT GGA CTT CAT CAG CAA CTG CAC GAG CTG GAG ACC TGC TTG      654
 T   G   L   H   Q   Q   L   H   E   L   E   T   C   L      123
CTG CAG GTA GTG GGA GAA TCT GCT GGG GCA ATT AGC               696
 L   Q   V   V   G   E   S   A   G   A   I   S               137
AGC CCT GCA CTG ACC TTG AGG TAC TTC CAG ATC CGT               738
 S   P   A   L   T   L   R   Y   F   Q   I   R               151
GTC TAC CTG AAA GAG AAG AAA TAC AGC TGT GCC TGG GAA           780
 V   Y   L   K   E   K   K   Y   S   C   A   W   E           165
GTT GTC AGA ATG GAA ATC AAA TCC TTG TTC TTA TCA ACA           822
 V   V   R   M   E   I   K   S   L   F   L   S   T           179
AAC ATG CAA GAA AGA CTG AGA AGT AAA GAT AGA GAC CTG GGC       864
 N   M   Q   E   R   L   R   S   K   D   R   D   L   G       193
TCA TCT TGA                                                  916
 S   S   *                                                   196
aatgattctcattcaaaagactccttattcggctttaatcacagaattgactg        971
tgactctggtcaattcaaatacctttgtcggtatataagccagtatgttaaaaagac  1026
aattagttctgcaaatactcagtcccctaagatgttatttttactcattatta     1081
ttaggttcaggggcatcagtcccctaagatgttatttttactcattatttatta     1081
ttcttacatttatcatatcatttatattcttatattcttatataacaaatgtttgc   1136
ctttacattgtattaagataacaaacatgttcaggatcc                    1176
```

```
EcoRI
gaattcgagattatcgtcactgcttcgcaatatggcgcaaaatgaccaac                          55
agcggttgattgatcaggtagagggggcgctgtaagcccgatgccag                             110
cattcctgacgacgatacggagctgctgcgcgattacgtaaagaagttattgaag                     165
catccctcgtcagtaaaagttaatctttcaacagctgtcataaagttgtcacgg                      220
                                                      XhoI
ccgagacttatagtcgctttgttttattttaatgtatttgctcgagaggttg                         275
             STII Leader peptide ->
aggtgatttt ATG AAA AAG AAT ATC GCA TTT CTT CTT GCA TCT                       318
           M   K   K   N   I   A   F   L   L   A   S                          11
                                                    IFNα2c ->
ATG TTC GTT TTT TCT ATT GCT ACA AAT GCC TAT GCA TGT GAT                      360
M   F   V   F   S   I   A   T   N   A   Y   A   C   D                         25
CTG CCT CAA ACC CAC AGC CTG GGT AGC AGG AGG ACC TTG ATG                      402
L   P   Q   T   H   S   L   G   S   R   R   T   L   M                         39
CTC CTG GCA CAG ATG AGG AGA ATC TCT CTT TTC TCC TGC TTG                      444
L   L   A   Q   M   R   R   I   S   L   F   S   C   L                         53
AAG GAC AGA CGT GAC TTT GGA TTT CCC CAG GAG GAG TTT GGC                      486
K   D   R   R   D   F   G   F   P   Q   E   E   F   G                         67
```

```
AAC CAG TTC CAA AAG GCT GAA ACC ATC CCT GTC CTC CAT GAG          528
 N   Q   F   Q   K   A   E   T   I   P   V   L   H   E           81
ATG ATC CAG CAG ATC TTC AGC ACA AAG TTC TAC GAC TCA              570
 M   I   Q   Q   I   F   S   T   K   F   Y   D   S               95
TCT GCT GCT TGG GAT GAG ACC CTC GAC AAA TTC TAC ACT              612
 S   A   A   W   D   E   T   L   D   K   F   Y   T              109
GAA CTC TAC CAG CTG AAT GAC CTG GAA GCC TGT GTG ATA              654
 E   L   Y   Q   L   N   D   L   E   A   C   V   I              123
CAG GGG GTG ACA GAG ACT CCC CTG ATG AAG GAG GAC                  696
 Q   G   V   T   E   T   P   L   M   K   E   D                  137
TCC ATT CTG GCT GTG AGG AAA TAC CAA TTC AGA ATC ACT CTC          738
 S   I   L   A   V   R   K   Y   Q   F   R   I   T   L          151
TAT CTG AAA GAG AAA AAG TAC AGC CCT TGT GCC TGG GAG GTT          780
 Y   L   K   E   K   K   Y   S   P   C   A   W   E   V          165
GTC AGA GCA GAA ATC ATG AGA TCT TTT TCT TTG TCA ACA AAC          822
 V   R   A   E   I   M   R   S   F   S   L   S   T   N          179
                                         PvuI    PstI
TTG CAA GAA AGT TTA AGA AGT AAG GAA tgataacgatcgtaactgc          868
 L   Q   E   S   L   R   S   K   E                              188
    HindIII
    agaagctt                                                     876
```

FIG. 2B (CONTD)

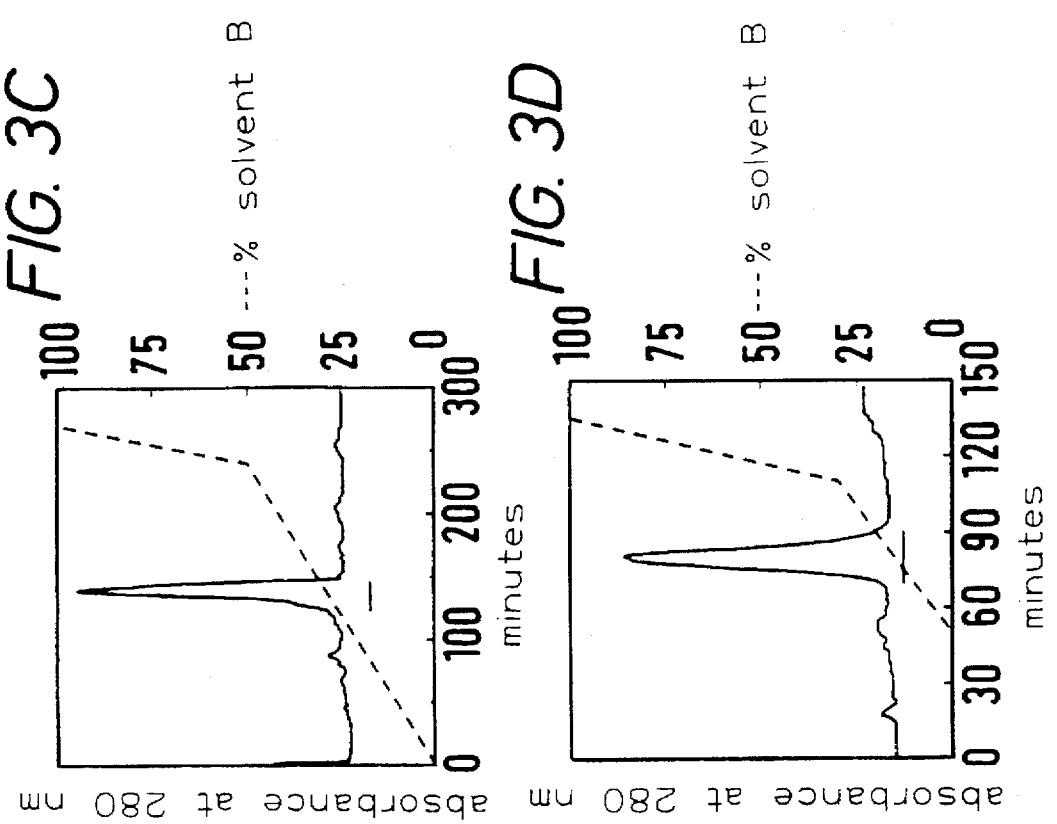
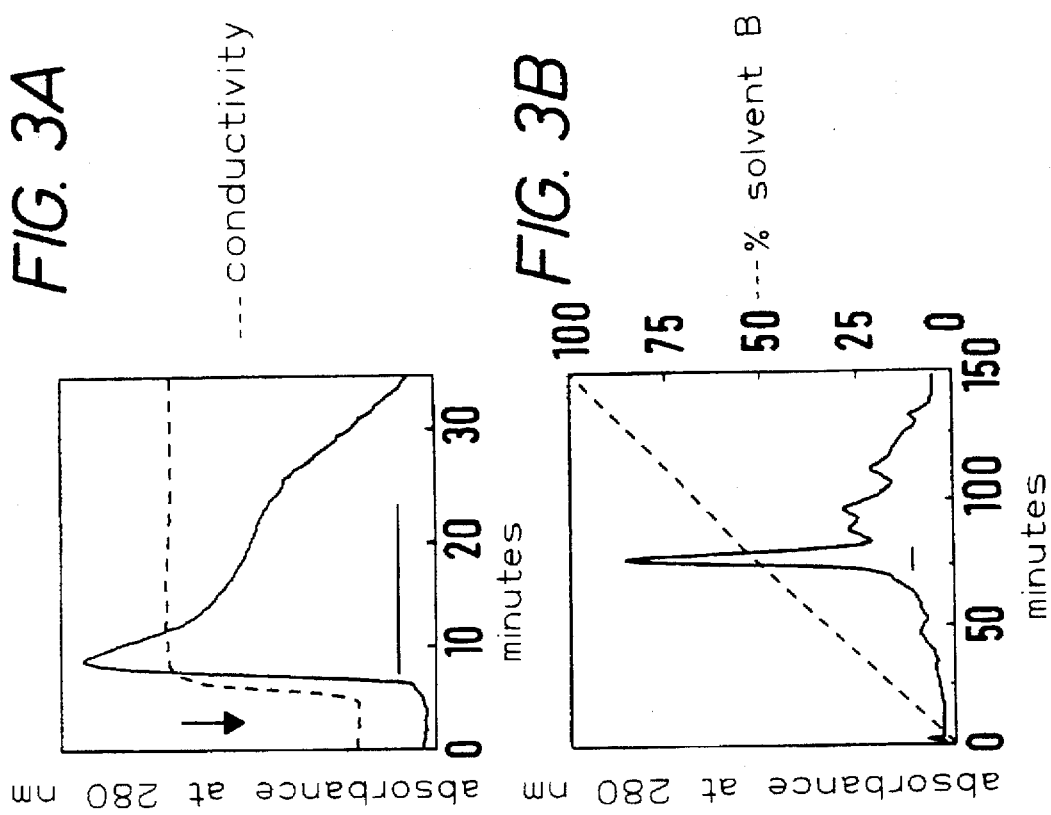

PROCESS AND VECTOR FOR EXPRESSING ALPHA-INTERFERON IN E. COLI

BACKGROUND OF THE INVENTION

1. Field of the Invention

The invention relates to a process for preparing interferon-alpha (herein "IFNα") by bacterial expression and subsequent isolation, an expression vector for this purpose and a process for purifying IFNα.

2. Description of Background Art

Processes for preparing IFNα by bacterial expression are known. The conventional process is based on cytoplasmic expression of the protein in *Escherichia coli*, in which the expressed IFNα is either present in the cell in insoluble form in so-called inclusion bodies or is found in the soluble fraction after the cell wall has been permeabilized or lysed (Thatcher & Panayotatos, *Methods Enzymol.* 119:166–177 (1986); Goeddel et al., *Nature* 287:411–416 (1980); Dworkin-Rastl et al., *Gene* 21:237–248 (1983)). Cytoplasmic expression does have some disadvantages, however. The synthesized protein is not correctly folded because reducing conditions prevail in the cytoplasm and the protein does not form the necessary disulfide bridges. Therefore, IFNα formed by cytoplasmic expression has to be oxidized and re-folded during preparation. This re-folding process is inefficient and leads to unwanted by-products, such as wholly or partially reduced forms, oligomers produced by intermolecular disulfide bridge building, and wrongly folded molecules formed by the cross-linking of improper disulfide bridges. These by-products are difficult to separate. A further problem with cytoplasmic expression is that the N-terminal methionine which is forms during translation is only partly cleaved from the IFNα synthesized intracellularly, and this form is undesirable. The resulting N-Met-IFNα is almost impossible to remove from the native IFNα.

A further disadvantage of the synthesis processes currently used is the use of promoters which, in the non-induced state, are not completely switched off. Moreover, such promoters have to be induced by the addition of chemicals and demonstrate an inefficient expression rates even in the induced state. An example of a commonly used inducible promotor is the trp-promotor from *Serratia marcescens*.

In order to overcome some of the above mentioned disadvantages and still employ the economical *E. coli* expression system, Breitling et al. attempted (Breitling et al., *Mol. Gen. Genet.* 217:384–391 (1989)) to express IFNα1 and an IFNα½ hybrid using a vector which enabled secretion of the IFN through the cell membrane into the periplasmic space. Breitling et al. used a promotor, ribosome binding site (RBS) and signal sequence from a bacterial staphylokinase gene (sak42D). They observed that 60–80% of the IFNα thus produced was secreted into the periplasmic space. However, the protein contained N-terminal amino acids as a result of the vector construction. These N-terminal amino acids do not occur in the corresponding native IFNα. A serious drawback of this expression system was the fact that the strains transformed with this construct did not remain genetically stable; the expression cassette was inactivated by the spontaneous insertion of an IS1 insertion element. The objective of providing an expression/secretion system in *E. coli* for preparing human IFNα has thus not been previously achieved.

A known expression/secretion cassette which has been successful in the expression of human growth factor receptor in *E. coli* was a construct from the promotor of alkaline phosphatase (phoA) and the signal sequence of the heat-stable enterotoxin II (STII) (Fuh et al., *J. Biol. Chem.* 265:3111–3115 (1990)).

Another problem in the production of recombinant IFNα in *E. coli* is the purification of the protein from the bacterial lysate. A number of processes are known (for example, Thatcher & Panayotatos, *Meth. Enzymol.* 119:166–177 (1986); European Patent No. EP-A 203,382)). In order to obtain the native folded protein it is preferable to use processes which do not require denaturation and precipitation steps. Such a process is described in European Patent No. EP-A 396,555. The process disclosed in EP-A 396,555 consists of the steps of performing immunoaffinity chromatography, reverse phase chromatography (RPC), cation exchange chromatography, concentration by ultrafiltration and gel filtration chromatography. This process, like other known processes, is based on the high selectivity of immunoaffinity chromatography in the first step. Prior to the present invention there was no known process for preparing highly purified IFNα, particularly IFNα2, which dispenses with both the denaturation/precipitation steps and immunoaffinity chromatography. However, a process of this kind is desirable for economic and technical reasons. There is a need for monoclonal antibodies for immunoaffinity chromatography and the cost of these reagents is high. Further, since the life of the antibody-coupled matrices is limited, a continuous supply of these antibodies is required. Moreover, there is a demand for IFNα proteins and simplifying the purification of this class of proteins will make purification less costly and less difficult.

SUMMARY OF THE INVENTION

The invention is directed to a more economical and efficient process for preparing IFNα, particularly IFNα2, by recombinant expression in *E. coli*. To achieve this goal, the problem of establishing an efficient and stable system for the expression/secretion of the protein into the periplasmic space or the culture medium has been solved. Moreover, the inventors have developed a process for highly purifying the expressed protein gently, without any denaturation/precipitation steps and without the need for immunoaffinity chromatography.

The inventors have solved these problems by means of the present invention. The establishment of a stable expression/secretion system for IFNα in *E. coli* was achieved by constructing a vector which contains the signal sequence (leader sequence) of heat stable enterotoxin II (STII) from *E. coli*, linked to the coding sequence for a mature human IFNα, preferably IFNα2. It is preferred that expression control is effected by means of the promotor of alkaline phosphatase from *E. coli* (phoA). It is further preferred that the construct comprise the ribosome binding site of the STII gene. Surprising results were achieved by providing a purification process for IFNα which consists of the steps of performing adsorption chromatography on silica gel, performing hydrophobic interaction chromatography (HIC), performing cation exchange chromatography and performing anion exchange chromatography.

Accordingly, one object of the invention is a process for preparing IFNα by expression in *E. coli*, comprising the steps of: expressing IFNα in cells comprising a vector in which the signal sequence of the gene for the heat stable enterotoxin II (STII) from *E. coli* is linked to a sequence which codes for mature human IFNα; and isolating the expressed IFNα.

Another object of the invention is a bacterial expression vector for expressing IFNα in *E. coli*, comprising a signal sequence of the STII gene operably linked to a sequence which codes for IFNα. It is preferred that the IFNα be mature human IFNα.

Yet another object of the invention is a process of purifying IFNα, comprising the steps of: performing chromatography on silica gel; performing hydrophobic interaction chromatography; performing cation exchange chromatography; and performing anion exchange chromatography.

BRIEF DESCRIPTION OF THE FIGURES

FIG. 1B) depicts a sequence of the EcoRI (destroyed)-BamHI part, which contains the phoA-promotor, STII leader and an IFNω1 gene (SEQ ID NO:8–9).

FIG. 2B) depicts a nucleotide sequence of the EcoRI-HindIII insert of pDH13 (SEQ ID NO:10–11).

FIGS. 3A–D depict graphs showing the chromatographic purification of IFNα2c, extracted from bacterial biomass. Optical absorbance is indicated.

FIG. 3A) depicts an elution curve of adsorption chromatography on silica gel. The arrow indicates elution with 800 mM tetramethylammonium chloride.

FIG. 3B) depicts an elution curve of hydrophobic interaction chromatography on phenyl-Sepharose™. Elution was carried out with a linear gradient of 0 to 100% of solvent B as indicated (----).

FIG. 3C) depicts an elution curve of sulphopropyl cation exchange chromatography. Elution was carried out with a gradient of 0 to 100% solvent B as indicated (----).

FIG. 3D) depicts an elution curve of anion exchange chromatography on DEAE Sepharose Fast Flow™. Elution was carried out with a gradient of 0 to 100% solvent B as indicated (----).

The bars under the main peaks in each chromatogram indicate the pools which contain IFNα2, which were collected and used for the subsequent steps.

Figure 4:
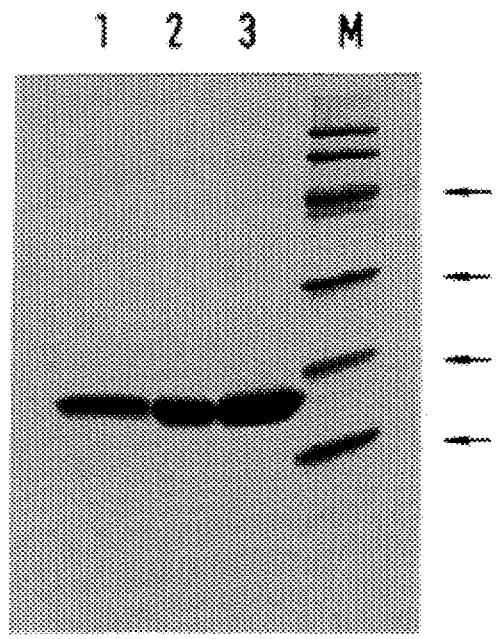

FIG. 4 depicts an SDS-PAGE of purified IFNα2c, stained with Coomassie blue. The numbers in the left-hand margin indicate the molecular weights of the standard proteins.

Figure 5A:
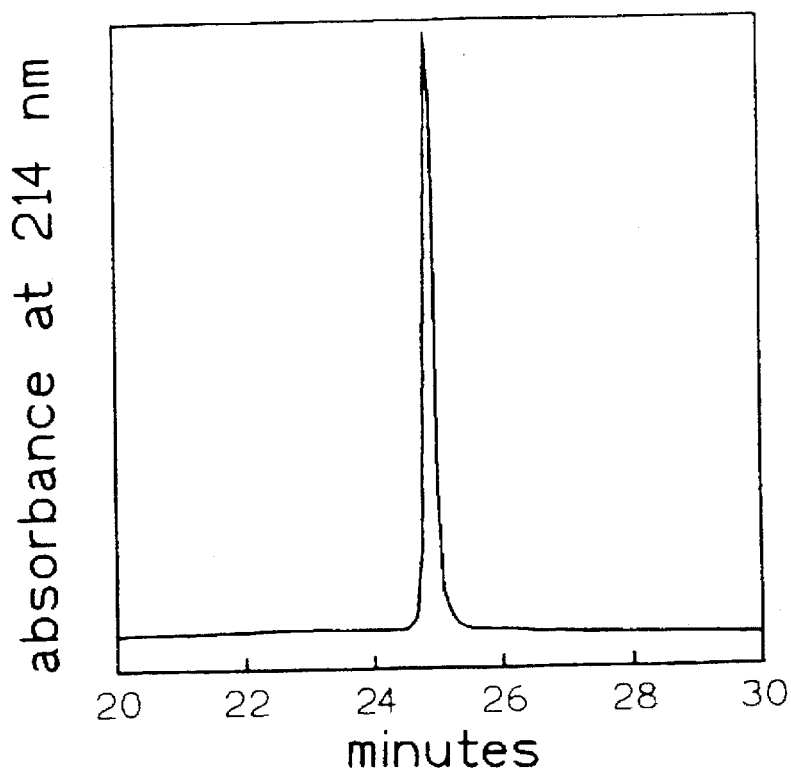
Figure 5B:
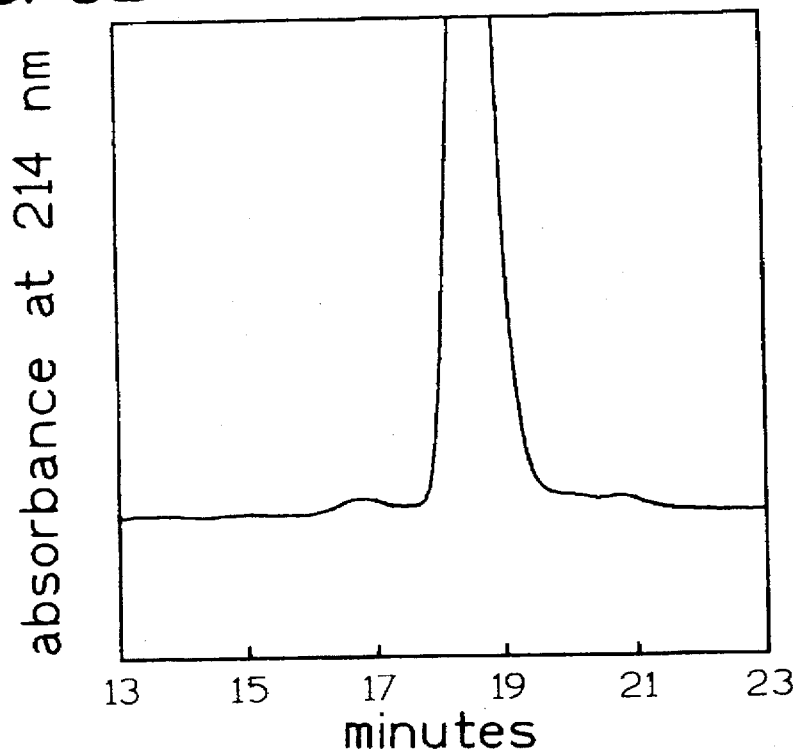

Lane 1: IFNα2c standard
Lane 2: 3 μg IFNα2c
Lane 3: 6 μg IFNα2c
Lane M: molecular weight standard FIGS. 5A–B depict chromatograms of purified IFNα2c separated by Reversed Phase HPLC (RP-HPLC). Optical absorbance was measured at 214 nm.

FIG. 5A) depicts an elution curve of IFNα2c with a linear gradient of 20–68% solvent B in 24 minutes.

FIG. 5B) depicts an elution curve of IFNα2c with a linear gradient of 45–53% solvent B in 30 minutes.

DETAILED DESCRIPTION OF THE PREFERRED EMBODIMENTS

The starting point for the construction of the vector may be a plasmid which is replicable in *E. coli*, such as the plasmid pAT153 (Twigg & Slierratt, *Nature* 283:216–218 (1980)), which is highly suitable for this purpose. Skilled artisans know of and may use other vectors and plasmids for gene expression in prokaryotes (see, for example, Sambrook et al., *Molecular Cloning—A Laboratory Manual*, Cold Spring Harbor Laboratory Press, Cold Spring Harbor, N.Y. (1989), for expression vectors and plasmids). A nucleotide sequence which codes for the signal peptide of the STII gene is known (Picken et al., *Infection and Immunity* 42:269–275 (1983); Lee et al., *Infection and Immunity* 42:264–268 (1983)). The skilled artisan will readily understand how to prepare variants of this sequence using methods known in the art such as, for example, by mutation (substitution, deletion, insertion, addition) without changing the basic properties thereof, and particularly to prepare nucleotide sequences which code for the same amino acid sequence of the signal peptide owing to the degeneracy of the genetic code (Sambrook et al., *Molecular Cloning—A Laboratory Manual*, Cold Spring Harbor Laboratory Press, Cold Spring Harbor, N.Y. (1989), especially Chapter 15). A whole series of sequences which code for members of IFNα family are known (Mantei et al., *Gene* 10:110 (1980); Streuli et al., *Science* 209:1343–1347 (1980); Goeddel et al., *Nature* 290:20–26 (1981)); the homology of the genes which code them is more than 70%. Other variants of these sequences can be found in nature or prepared from the known sequences by methods known in the art, e.g., by mutagenesis (see Sambrook et al., *Molecular Cloning—A Laboratory Manual*, Cold Spring Harbor Laboratory Press, Cold Spring Harbor, N.Y. (1989), especially Chapter 15).

As used herein the term "IFNα" refers generally to any IFNα amino acid or nucleic acid sequence including, for example, known sequences and those variants whose genes are characterized by a high degree of homology with the known sequence and which code for biologically active IFNα and compounds having substantially the same biologically activity as known forms of IFNα.

Herein the terms "process" and "method" are used interchangeably.

It is preferred in the invention that the sequence which codes for IFNα2, particularly IFNα2c (Dworkin-Rastl et al., *Gene* 21:237–248 (1983); Bodo & Maurer-Fogy, in: *The Biology of the Interferon System* 1985 (Stewart & Scliellekens), 59–64, Elsevier Scientific Publishing Co., Amsterdam (1985) be used. It is more preferred in the methods of the invention that the IFNα2 is IFNα2 having an amino acid sequence:

Cys Asp Leu Pro Gln Thr His Ser Leu Gly Ser Arg Arg Thr

Leu Met Leu Leu Ala Gln Met Arg Arg Ile Ser Leu Phe Ser

Cys Leu Lys Asp Arg Arg Asp Phe Gly Phe Pro Gln Glu Glu

Phe Gly Asn Gln Phe Gln Lys Ala Glu Thr Ile Pro Val Leu

His Glu Met Ile Gln Gln Ile Phe Asn Leu Phe Ser Thr Lys

-continued

Asp Ser Ser Ala Ala Trp Asp Glu Thr Leu Leu Asp Lys Phe

Tyr Thr Glu Leu Tyr Gln Gln Leu Asn Asp Leu Glu Ala Cys

Val Ile Gln Gly Val Gly Val Thr Glu Thr Pro Leu Met Lys

Glu Asp Ser Ile Leu Ala Val Arg Lys Tyr Phe Gln Arg Ile

Thr Leu Tyr Leu Lys Glu Lys Lys Tyr Ser Pro Cys Ala Trp

Glu Val Val Arg Ala Glu Ile Met Arg Ser Phe Ser Leu Ser

Thr Asn Leu Gln Glu Ser Leu Arg Ser Lys Glu (SEQ ID NO: 5)

It is most preferred that in the constructs of the invention that the nucleotide sequence encoding IFNα2 encodes IFNα2 having the amino acid sequence of SEQ ID NO:5.

It is also preferred that in the methods and constructs of the invention the IFNα2 is IFNα2 encoded by a polynucleotide having the sequence:

molecules since certain of these molecules will have IFN functions. It is a matter of routine practice for skilled artisans to mutate or select DNA sequences that are homologous to those in SEQ ID NOS:6 and 7. Techniques are known in the art for determining the degree of homology between DNA sequences (Beltz et al., *Meth. Enzymol.* 100:266–285 (1983)). Nucleic acid hybridization, such as filter hybridization is a common technique used to determine homology. Beltz et al., *Meth. Enzymol.* 100:266–285 (1983) teach washing conditions, probe length and guanidine/cytosine content, ionic strength of the wash and wash temperatures useful for filter hybridization homology determination. Moreover, skilled artisans can determine the level of DNA-DNA hybridization using methods known in the art (Owen et al., *Chem. Meth. Bact. Systemat*, pp. 67–93 (1985)). Methods for determining nucleic acid homology are also known in the art (Kafatos et al., *Nucl. Acids Res.* 7(6):1541–1552 (1979). Sequencing of DNA fragments followed by direct comparison of the homology between the fragments can also be performed.

Accordingly, it is further preferred that in the methods and constructs of the invention the IFNα2 is encoded by a nucleotide sequence that is at least about 70% homologous

TGT GAT CTG CCT CAA ACC CAC AGC CTG GGT AGC AGG AGG ACC

TTG ATG CTC CTG GCA CAG ATG AGG AGA ATC TCT CTT TTC TCC

TGC TTG AAG GAC AGA CGT GAC TTT GGA TTT CCC CAG GAG GAG

TTT GGC AAC CAG TTC CAA AAG GCT GAA ACC ATC CCT GTC CTC

CAT GAG ATG ATC CAG CAG ATC TTC AAT CTC TTC AGC ACA AAG

GAC TCA TCT GCT GCT TGG GAT GAG ACC CTC CTA GAC AAA TTC

TAC ACT GAA CTC TAC CAG CAG CTG AAT GAC CTG GAA GCC TGT

GTG ATA CAG GGG GTG GGG GTG ACA GAG ACT CCC CTG ATG AAG

GAG GAC TCC ATT CTG GCT GTG AGG AAA TAC TTC CAA AGA ATC

ACT CTC TAT CTG AAA GAG AAG AAA TAC AGC CCT TGT GCC TGG

GAG GTT GTC AGA GCA GAA ATC ATG AGA TCT TTT TCT TTG TCA

ACA AAC TTG CAA GAA AGT TTA AGA AGT AAG GAA (SEQ ID NO: 6).

It is more preferred that in the methods and constructs of the invention the IFNα2 is IFNα2 encoded by the nucleotide sequence of SEQ ID NO:6.

Skilled artisans will readily understand that IFNα species that are encoded by DNA sequences having homology to the sequences in SEQ ID NOS:6 and 7 will be useful IFN with the nucleotide sequence of SEQ ID NO:6, particularly a nucleotide sequence which codes for a protein having an IFNα activity.

It is also preferred that in the methods and constructs of the invention the IFNα2 is IFNα2 encoded by a polynucleotide having the sequence:

GAATTCGAGATTATCGTCACTGCAATGCTTCGCAATATGGCGCAAAATGACCAACAG

CGGTTGATTGATCAGGTAGAGGGGGCGCTGTACGAGGTAAAGCCCGATGCCAGCATT

-continued

```
CCTGACGACGATACGGAGCTGCTGCGCGATTACGTAAAGAAGTTATTGAAGCATCCT

CGTCAGTAAAAAGTTAATCTTTTCAACAGCTGTCATAAAGTTGTCACGGCCGAGACT

TATAGTCGCTTTGTTTTTATTTTTTAATGTATTTGCTCGAGAGGTTGAGGTGATTTT

ATG AAA AAG AAT ATC GCA TTT CTT CTT GCA TCT ATG TTC GTT

TTT TCT ATT GCT ACA AAT CCC TAT GCA TGT GAT CTG CCT CAA

ACC CAC AGC CTG GGT AGC AGG AGG ACC TTG ATG CTC CTG GCA

CAG ATG AGG AGA ATC TCT CTT TTC TCC TGC TTG AAG GAC AGA

CGT GAC TTT GGA TTT CCC CAG GAG GAG TTT GGC AAC CAG TTC

CAA AAG GCT GAA ACC ATC CCT GTC CTC CAT GAG ATG ATC CAG

CAG ATC TTC AAT CTC TTC AGC ACA AAG GAC TCA TCT GCT GCT

TGG GAT GAG ACC CTC CTA GAC AAA TTC TAC ACT GAA CTC TAC

CAG CAG CTG AAT GAC CTG GAA GCC TGT GTG ATA CAG GGG GTG

GGG GTG ACA GAG ACT CCC CTG ATG AAG GAG GAC TCC ATT CTG

GCT GTG AGG AAA TAC TTC CAA AGA ATC ACT CTC TAT CTG AAA

GAG AAG AAA TAC AGC CCT TGT GCC TGG GAG GTT GTC AGA GCA

GAA ATC ATG AGA TCT TTT TCT TTG TCA ACA AAC TTG CAA GAA

AGT TTA AGA AGT AAG GAA TGATAACGATCGTAACTGCA  (SEQ ID NO: 7).
```

It is more preferred that in the methods and constructs of the invention the IFNα2 is IFNα2 encoded by the nucleotide sequence of SEQ ID NO:7.

It is further preferred that in the methods and constructs of the invention the IFNα2 is encoded by a nucleotide sequence that is at least about 70% homologous with the nucleotide acid of SEQ ID NO:7, particularly a nucleotide sequence which codes for a protein having an IFNα activity.

It is also preferred in the invention that the E. coli alkaline phosphatase (phoA) promotor is used for controlling expression and it is also preferred that the ribosome binding site of the STII gene be integrated into the gene expression constructs, plasmids and vectors of the invention. The sequence of the phoA-promotor is disclosed by Chang et al., Gene 44:121–125 (1986); Shuttleworth et al., Nucl. Acids Res. 14:8689 (1986) and that of the STII ribosome binding site is disclosed by Picken et al., Infection and Immunity 42:269–275 (1983); and Lee et al., Infection and Immunity 42:264–268 (1983)). The promotor and ribosome-binding site sequences are operably linked in the expression construct and are capable of mediating expression of the IFN gene of interest. The skilled artisan can easily produce equivalent variants from the sequences in the expression vector, particularly the promotor and ribosome-binding site sequences.

Construction of the vector, transformation of suitable E. coli strains, fermentation and extraction can be carried out using methods known in the art (Sambrook et al., Molecular Cloning—A Laboratory Manual, Cold Spring Harbor Laboratory Press, Cold Spring Harbor, N.Y. (1989)). For example, the E. coli strain W3110 (E. coli K12 Wild type f⁻, λ⁻, IN (rrnD-rrnE)1) is suitable for expression and is preferred in the constructs and methods of the invention. The preliminary bacterial culture can be grown in LB medium and the main culture can be made, with monitoring of the supply of oxygen and nutrients, up to an $OD_{546}$ of 250 to 280.

Surprisingly, by linking the STII signal sequence to the IFNα gene, it was possible to establish a stable expression/secretion system, which had not been possible with the sak42D leader/IFNα combination known in the art. It is preferred that the constructs of the invention be expressed under the control of the phoA promotor. The integration of the ribosome binding site of the STII gene is a particularly preferred construct useful for expression. Expression can reliably be controlled by, for example, monitoring the phosphate concentration in the medium (phosphate deficiency, activates the phoA promotor); in the inactivated state there is no detectable basal expression. Additional chemicals do not need to be added for activation/induction; the expression rate in the activated state is high. The synthesized protein is secreted in large amounts into the periplasmic space. The secreted protein is correctly folded, contains the authentic N-terminus and the correct disulfide bridges. The SDS gel analysis of expression in E. coli W3110 showed that about 30–50% of the synthesized IFNα had been correctly processed; this corresponds to virtually all the secreted protein.

The initial extraction methods useful in the invention can be those known in the art (see, for example, Sambrook et al., *Molecular Cloning—A Laboratory Manual*, Cold Spring Harbor Laboratory Press, Cold Spring Harbor, N.Y. (1989)). However, an extraction method which is preferred in the invention involves suspending acid-inactivated biomass in dilute acetic acid with the aid of a homogenizer, adding polyethyleneamine, preferably in a concentration of about 0.25% (w/v), adjusting the mixture to an alkaline pH, preferably about pH 10, stirring the mixture and then removing the bacteria by centrifuging.

The invention provides a multistep chromatographic purification process. A preferred purification process having four chromatographic steps, namely performing adsorption chromatography on silica gel, hydrophobic interaction chromatography, cation and anion exchange chromatography, is provided in the invention. It is more preferred that the four chromatographic steps be temporally ordered thusly: performing adsorption chromatography on silica gel, followed by hydrophobic interaction chromatography, followed by cation and then anion exchange chromatography.

Type 953W gel made by Grace is preferred as the gel layer for the silica chromatography. It is also preferred that the flow rate of the column be about 25 ml/min, and that the column be equilibrated to a pH of about 7.5 with buffer, particularly Tris-HCl. A buffer, especially about 500–1500 mM tetramethylammoniumchloride (herein "TMAC"), and particularly about 800 mM TMAC, is preferred as an eluant.

For the hydrophobic interaction chromatography it is preferred that the gel bed comprises phenyl Sepharose™. It is further preferred that samples be applied in the presence of about 20% ammonium sulphate and that the column be equilibrated with a buffer, such as Tris-HCl, containing about 30% ammonium sulphate. The IFNα is preferably eluted with a linear gradient having a final concentration of about 30% ethylene glycol.

Cation exchange chromatography may be used to purify the above-mentioned eluted material. It is preferred that the cation exchange chromatography be carried out using a sulphopropyl ion exchange resin, such as, for example Toyopearl™ TSK SP 5PW (Tosohaas). The pH of the eluate can adjusted by dialysis with Na-succinate, preferably at a concentration of about 20 mM (about pH 5.0), prior to loading onto the ion exchange resin. It is preferred that the samples be applied at a pH of 3 to 5, preferably pH 3 and the column can be equilibrated to a more preferred pH of 5. IFNα is preferably eluted with a linear common salt gradient by the addition of about 10% ethylene glycol.

The preferred gel bed used for anion exchange chromatography comprises DEAE-Sepharose™, such as DEAE Sepharose Fast Flow™ (Pharmacia). The sample application and elution is preferably carried out at above about pH 5.5 to 6.0, particularly at about pH 5.8. A linear common salt gradient with the addition of about 0.1% Tween 20 is preferred for elution. It is most preferred that the elution be carried out using about 10 mM bisTris, about 500 mM NaCl, about 0.1% Tween 20 at about pH 5.8. It is preferred that the elution flow rate be about 5 ml/min.

Any one of the chromatographic steps can be modified using techniques known in the an once the disclosed invention is understood by the skilled artisan (see, for example, Thatcher & Panayotatos, *Meth. Enzymol.* 119:166–177 (1986); EP-A 203,382). These modifications are within the spirit of the invention. For instance, it is within the technical capabilities of the skilled artisan to replace one or more gel materials with substantially equivalent materials or substantially functionally equivalent materials based on the same separation principles, without any inventive activity, and in this way to perform the process according to the invention.

Following purification, samples may be analyzed using reversed phase HPLC. Skilled artisans will readily be able to utilize reversed phase HPLC to analyze the composition and purity of the samples. It is most preferred that the samples be analyzed using a column comprising a bed with a particle size of about 5 μm, particularly a BakerBond-WP-C18 column (250×4.5 mm, particle size 5 μm). Tryptic peptides can be generated using methods known in the art and analyzed by reversed phase HPLC. It is preferred that the tryptic peptides be analyzed using a column comprising a bed with a particle size of about 4 μm, such as, for example, a Merck Supersphere™ 120-4 C-18 column (125×4.5 mm, particle size 4 μm). Standard solvents known in the art can be used for chromatography. It is preferred that the samples be chromatographed using solvent A (trifluoroacetic acid in water) and solvent B (trifluoroacetic acid in acetonitrile).

Further analysis of the purified IFNα samples can be performed by gel electrophoresis, especially an SDS polyacrylamide gel under standard reducing conditions, particularly a 16% gel. Samples may be reduced with any standard protein reducing agent, such as dithiothreitol, before electrophoresis.

The IFNα content of various samples obtained during purification may be quantitated by any technique known in the art for protein quantitation, particularly immunological techniques, and especially by ELISA. Using sandwich ELISA and the monoclonal antibodies OMG-2 and MG-7 (Adolf, G. R., *Virology* 175:410–417 (1990) the amount of IFNα in a sample can be conveniently quantitated.

All of the references cited herein are incorporated by reference herein in their entirety.

Having now generally described this invention the same will better be understood by reference to certain specific examples which are included for the purposes of illustration and are not intended to limit the invention unless otherwise specified.

EXAMPLES

Example 1

Preparation of the pDH13 Expression Vector and the Transformation of Bacterial Cells A. General Methods Restriction digestion of DNA with restriction endonucleases, filling-in reactions, phenol extraction and precipitation of DNA, agarose gel electrophoresis and elution of DNA from agarose gels, ligation of DNA molecules, transformation of bacteria and plasmid isolation from bacteria are standard procedures and were carried out as described by Sambrook et al., *Molecular Cloning—A Laboratory Manual*, Cold Spring Harbor Laboratory Press, Cold Spring Harbor, N.Y. (1989).

Figure 1A:
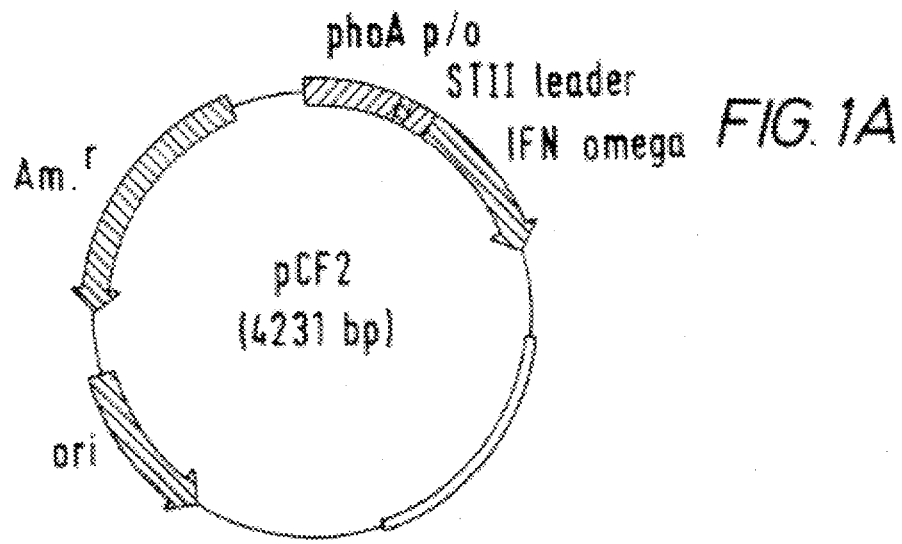
FIG. 1A) depicts a gene map of pCF2. The EcoRI-BamHI fragment of pAT153 was replaced by the expression cassette for IFNω1.

B. Plasmids pCF2 pCF2 was prepared from the plasmid pAT153 (Twigg & Slierratt, *Nature* 283:216–218 (1980)). It contains the promotor of alkaline phosphatase from *E. coli* (phoA) (Chang et al., *Gene* 44:121–125 (1986); Shuttleworth et al., *Nucl. Acids Res.* 14:8689 (1986)), the coding region of the STII leader peptide (Picken et al., *Infec-* tion and Immunity 42:269–275 (1983); Lee et al., Infection and Immunity 42:264–268 (1983)) and the gene for human IFNω1 (Hauptmann et al., *Nucl. Acids Res.* 13:4739–4749 (1985)). FIG. 1 shows the gene map of pCF2 and the sequence of the relevant region comprising the PhoA and STII gene expression control sequences and the IFN sequence.

pER21/1 pER21/1 is a bacterial expression vector for IFNα2c (EPO 115,613).

C. Oligonucleotides

Table 4 depicts the oligonucleotides used in PCR reactions employed in the construction of the vectors in Example 1. The oligonucleotide sequences are depicted in the 5'→3' orientation. In the sections which follow the oligonucleotides are referred to by their "EBI" number (see Table 4).

1. Cloning of the PCR Product (pDH9)

Bluescribe M13+ (Stratagene, San Diego, Calif., U.S.A.) was doubly cut with HindIII and EcoRI and the large fragment was gel-purified with a 1.2% agarose gel. 10 ng of Bluescribe™ M13+ DNA and 50 ng of PCR product cut with EcoRI/Hind III were ligated in 10 µl of solution containing 50 mM Tris-HCl, pH 7.6, 10 mM $MgCl_2$, 20 mM dithiothreitol, 1 mM ATP, 50 mg/ml bovine serum albumin (BSA) and 2 units of T4-DNA-ligase (NEN), for 1 hour at 0° C. and for 3 hours at ambient temperature. 8 µl of this solution were used for the transformation of competent *E. coli* cells of the strain JM 101 (*E. coli* K12, SupE, thi, Δ(lac-proAB), (F', traD36, proAB, lacIZΔM15]).

A clone was selected, the DNA was isolated and the expression cassette sequenced. The sequence corresponded precisely to the sequence expected theoretically (FIG. 2). The plasmid was designated pDH9.

TABLE 4

| | | |
|---|---|---|
| EBI-2787: | CGTCTTCAAGAATTCGAGATTATCG | SEQ ID NO:1 |
| EBI-2799: | GGCAGATCACATGCATAGGCATTTGTAGCAATAG | SEQ ID NO:2 |
| EBI-2798: | ATGCCTATGCATGTGATCTGCCTCAAACCCACAGC | SEQ ID NO:3 |
| EBI-2797: | GACTTCAGAAGCTTCTGCAGTTACGATCGATCGTTA TCATTCCTTACTTCTTAAACTTTC | SEQ ID NO:4 |

D. Preparation of the Expression Cassette from the phoA Promotor, IFNα2c Sequence and STII Leader Sequence in a Two-Step PCR pER21/1 (EPO 115,613) DNA was linearized with HindIII, pCF2-DNA with PvuI. The method used hereinafter is described as SOE-PCR ("splicing by overlap extension", Ho et al., *Gene* 77:51–59 (1989)).

PCR 1a (Amplification of the IFNα2c gene): 100 ng of linearized pER21/1 DNA, 25 pmol EBI-2797 and 25 pmol EBI-2798 were subjected to thermocycles in 50 µl of buffer which contained 50 mM KCl, 10 mM Tris-HCl, pH 8.3, 1.5 mM $MgCl_2$, 0.01% gelatine, 0.2 mM dATP, 0.2 mM dGTP, 02. mM dCTP, 0.2 mM dTTP and 1.25 units of Taq-polymerase, in a Perkin-Elmer Cetus Thermocycler TC-1. After 3 minutes' incubation at 94° C., 10 cycles were performed (stage 1: 40 seconds at 94° C., stage 2: 30 seconds at 55° C., stage 3: 90 seconds at 72° C.).

PCR 1b (Amplification of phoA-promotor plus STII leader sequence): 100 ng of linearized pCF2-DNA, 25 pmol EBI 2787 and 25 pmol EBI 2799 were subjected to thermocycles in the same buffer and under the same conditions as described under PCR 1a.

The resulting DNA fragments of PCR 1a (540 bp) and PCR 1b (374 bp) were gel-purified (1.2% low gelling type agarose in TBE buffer, 1×TBE: 10.8 g Tris/l, 5.5 g boric acid/l, 0.93 g EDTA/l). The agarose section containing the DNA fragment of PCR 1a was excised and the agarose was melted by adding 100 µl of $H_2O$ and heating to 70° C.

PCR 2: 5 µl of each agarose/DNA solution were combined and subjected to thermocycles in 100 µl of solution containing 50 pmol of EBI-2787 and EBI-2797. The buffer was the same as described under PCR 1a. The thermocycle equipment was programmed so that a delay period of 5 minutes at 94° C. was followed by 20 cycles (step 1: 40 seconds at 94° C., step 2: 30 seconds at 55° C., step 3: 5 minutes at 72° C.; step 3 was extended by 5 seconds in each new cycle). After amplification the DNA was purified by phenol/chloroform extraction and ethanol precipitation. The PCR product was dissolved and cut with HindIII and EcoRI in the corresponding buffers.

2. Construction of the Expression plasmid pDH13 pAT153 was doubly cut with SspI and PstI and the large fragment was isolated. pDH9 was cut with EcoRI and the ends were filled using the Klenow fragment of DNA polymerase 1 and the 4 dNTPs. After phenol extraction and precipitation of the linear pDH9-DNA, this DNA was cut with PstI and the fragment containing the phoA-promotor, the STII leader sequence and the IFNα2c gene was isolated from a 1% agarose gel.

Figure 2A:
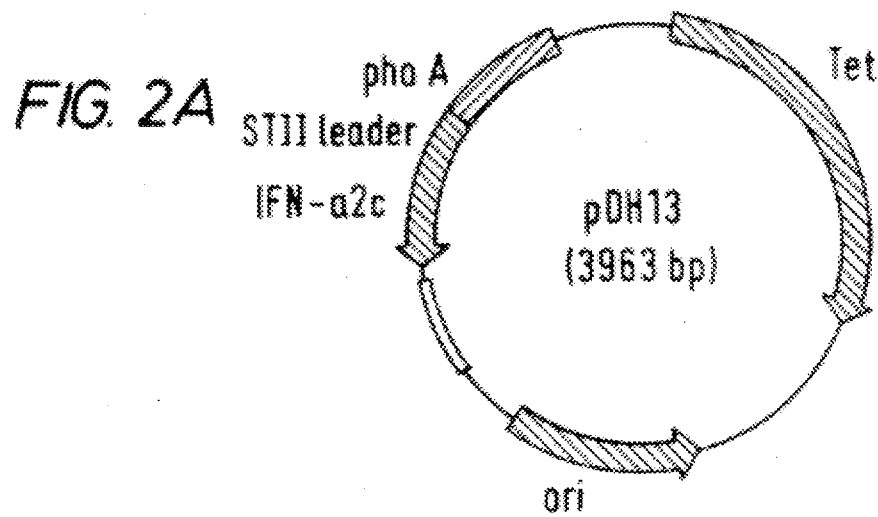
FIG. 2A) depicts a gene map of the plasmid pDH13. The SspI-PstI fragment of pAT153 was replaced by the IFNα2c expression cassette (EcoRI-PstI fragment of 2B). The β-lactamase gene is destroyed.

10 ng of pAT153×SspI×PstI and 30 ng of the fragment containing the expression cassette were ligated in 10 µl of solution for 5 hours at ambient temperature. 5 µl of this mixture were used to transform competent *E. coli* bacteria of the strain HB101. The selection of the transformed bacteria was carried out on LB agar plates (10 g tryptone/l, 5 g yeast extract/l, 5 g NaCl/l, 15 g bacto-agar/l), containing 10 µg/ml tetracycline. A gene map of pDH13 and the sequence of the relevant region is shown in FIGS. 2A–B.

Plasmid DNA from various colonies thus obtained was isolated and checked for correct composition by restriction analysis. A plasmid was selected and designated pDH13. The plasmid pDH13 was used for transforming *E. coli* W3110 (*E. coli* K12 . Wild type, f⁻, γ⁻, IN (rrnD-rrnE)1).

Example 2

Fermentation

A. Preliminary Culture 700 ml of autoclaved LB medium (10 g bacto-tryptone/l, 5 g bacto-yeast extract/l, 10 g NaCl/l, pH 7.0), containing 5 mg/l tetracycline, were inoculated in a 2 liter glass vessel from a stock culture so as to obtain an $OD_{546}$ of 0.01. The culture was incubated for 10 hours at 37° C. with vigorous stirring (800 rpm) and aeration (5 fermented volumes per minute (vvm)).

B. Main Culture
Composition of medium
In the fermenter:
1.21 g/l $(NH_4)_2HPO_4$
3.96 g/l $(NH_4)_2SO_4$ 6.53 g/l K$_2$HPO$_4$
1.23 g/l MgSO$_4$×7 H$_2$O
0.32 g/l NaCl
0.25 g/l NH$_4$Cl
1.0 g/l Na$_3$-citrate×2 H$_2$O
1.0 ml/l Trace element concentrate
12.5 g/l Glucose
20 mg/l Thiamine-HCl
50 mg/l L-tryptophan
100 mg/l L-leucine
50 mg/l L-methionine
5 mg/l Tetracycline Trace element concentrate (amounts per 100 ml):

3.35 g FeCl$_3$×6 H$_2$O
1.09 g ZnSO$_4$×7 H$_2$O
0.267 g CoCl$_2$×6 H$_2$O
0.267 g Na$_2$MnO$_4$×2 H$_2$O
0.221 g CuSO$_4$×5 H$_2$O
0.333 g H$_3$BO$_3$
1.37 g MnSO$_4$×H$_2$O
10 ml HCl conc. H$_2$O add 100 ml Feeding during fermentation (amounts based on volume of fermenter):

350 g/l Glucose
3.70 g/l MgSO$_4$×7 H$_2$O
175 mg/l Thiamine-HCl
0.50 g/l L-tryptophan
4.0 g/l L-leucine
2.0 g/l L-methionine Metered addition of antifoamers during fermentation (based on fermenter volume):

1.0 ml/l UCON LB625

Salts ((NH$_4$)$_2$PO$_4$, (NH$_4$)$_2$SO$_4$, K$_2$HPO$_4$, NaCl, NH$_4$Cl and Na-citrate) were sterilized in a fermenter. Trace elements, MgSO$_4$ glucose, thiamine, L-tryptophan, L-leucine, L-methionine and tetracycline were added aseptically after cooling so as to obtain a starting volume of 7 liters. 600 ml of the preliminary culture were automatically inoculated into the fermenter. The fermentation conditions were: stirring at 1000 rpm, aeration of 1 vvm, 0.3 bar backpressure, a temperature of 37.0°±0.1° C., the pH being maintained at 6.7±0.1 using NH$_3$ and H$_2$SO$_4$. The concentration of dissolved oxygen was kept above 15% air saturation by aerating with oxygen-enriched air as necessary (at 0.3 bar backpressure). After the glucose initially present had been consumed, a feeding process was started up which was automatically triggered by the oxygen concentration and contained glucose, thiamine, MgSO$_4$, L-tryptophan, L-leucine and L-methionine. The feeding rate started at 2.5 g/l/h and was increased continuously to 5.0 g/l/h within 24 hours and kept constant until the end of the fermentation process.

Fermentation was ended when a total quantity of 350 g/l of glucose had been added. At this time, a typical optical density of 250 to 280 was achieved at 546 nm.

To inactive the biomass the mixture was cooled to about 10° C. and at the same time the pH was adjusted to 2.0 using H$_2$SO$_4$. The biomass was separated off by centrifuging and stored frozen at −70° C.

Example 3

Extraction of IFN

Acid-inactivated biomass (about 0.5 kg) was suspended in 500 ml of 1% acetic acid using a Polytron homogenizer and the mixture was stirred for 1 hour at 0° C. Polyethyleneimine (50% stock solution, Serva, Heidelberg) was added to give a final concentration of 0.25% (w/v). The suspension was adjusted to a pH of 10.0 using 5N NaOH and stirred for a further 2 hours at 0° C. After the pH had been adjusted to 7.5 using 5N HCl, the bacteria were separated off by centrifuging at 17,000×g (Beckman J2-21 centrifuge). The average extraction yield was 29.3±5.9% of the total content of IFNα2c.

Example 4

Chromatographic Purification of IFN

A. Adsorption Chromatography on Silica Gel

The supernatant containing IFNα, after separation of the bacterial pellet in Example 3, was loaded onto a silica gel column (Grace, silica type 953W; 35 mg protein/ml column material, flow rate 25 ml/min), which had been equilibrated with 20 mM Tris-HCl, pH 7.5. The column was washed with 30 column volumes of starting buffer, then a washing step with 20 mM Tris-HCl, 100 mM tetramethylammonium chloride (TMAC), pH 7.5, was carried out. IFNα2c could be eluted by increasing the TMAC concentration to 800 mM TMAC (FIG. 3A).

B. Hydrophobic Interaction Chromatography

The material eluted from the silica gel column was adjusted to an ammonium sulphate concentration of 20% (w/v) by the addition of solid (NH$_4$)$_2$SO$_4$ and loaded onto a phenyl Sepharose™ column (phenyl toyopearl, 650S, Tosohaas) which had been equilibrated with 20 mM Tris-HCl, 30% ammonium sulphate. IFNα2c was eluted with a linear gradient from 100% loading conditions to 100% 20 mM Tris-HCl, 30% ethyleneglycol, pH 7.5, at a flow rate of 15 ml/min. The purity of the IFNα pool was 71±15%.

C. Cation Exchange Chromatography

The eluate of the hydrophobic interaction chromatography was adjusted by extensive dialysis to 20 mM Na-succinate, pH 5.0. The final pH was adjusted to 3.0 with HCl, before the sample was loaded onto a sulphopropyl-ion exchange resin (Toyopearl™ TSK SP 5PW, Tosohaas), equilibrated with 20 mM Na-succinate, pH 5.0. IFNα2c was eluted from the column with a linear gradient from 100% loading conditions to 100% 20 mM Na-succinate, 500 mM NaCl, 10% ethyleneglycol, pH 5.5 (solvent B) at a flow rate of 6 ml/min. The IFNα2c eluted from this column routinely had a purity higher than 95%.

D. Anion Exchange Chromatography

The IFNα pool was dialyzed against 10 mM bisTris, pH 5.8, and loaded onto a DEAE Sepharose™ (DEAE Sepharose FastFlow, Pharmacia) which was equilibrated with the same buffer. The elution of IFNα2c was carried out with a linear gradient on 10 mM bisTris, 500 mM NaCl, 0.1% Tween™ 20 (polyoxyethylene sorbitas monolaurate), pH 5.8 (solvent B), flow rate 5 ml/min.

Example 5

Analysis of the IFNα2c Preparations

A. Reversed Phase HPLC

Intact IFNα2c was analyzed at 30° C. with a BakerBond-WP-C18 column (250×4.5 mm, particle size 5 µm). A Merck Supersphere™ 120-4 C-18 column (125×4.5 mm, particle size 4 µm) was used at 37° C. to separate tryptic peptides. The samples were chromatographed using solvent A, 0.1% trifluoroacetic acid in water, and B, 0.1% trifluoroacetic acid in acetonitrile and using the gradients as described in the relevant legend to the FIG. 3.

B. SDS-Polyacrylamide Gel Electrophoresis

IFNα2c samples were analyzed on 16% SDS polyacrylamide gels under standard reducing conditions. Samples were reduced with dithiothreitol before electrophoresis. Protein bands were visualized with Coomassie blue staining.

C. Quantifying IFNα2c by ELISA

The IFNα2c content of various samples obtained during purification was determined by sandwich ELISA with the monoclonal antibodies OMG-2 and MG-7 (Adolf, G. R., *Virology* 175:410–417 (1990)).

Results

Using the extraction process described in Example 3 it was possible to extract 29.3±5.9% of all the IFNα2c detectable in the biomass. This corresponded to an observed processing level of about 30–50%. The extract from the biomass contained 4.5±1.8% IFNα2c, based on a measurement of total protein. Silica adsorption chromatography led to an IFNα2c pool with an average purity of 16.7±4.4%. Phenyl Sepharose™ chromatography with a yield of 93.2±7.3% yielded an IFNα2c with a purity of 71.2±15.5%. Sulphopropyl ion exchange chromatography produced a yield of 70.9±14.8% and a purity of 97.6±4.6%. Another step, namely DEAE ion exchange chromatography, resulted in 100% pure IFNα2c, in a yield of 86.9±9.2%, as detailed hereinafter. The data from 6 different purifications are shown in Tables 5 (yields) and 6 (IFNα2c content). FIG. 3 shows characteristic chromatograms of each purification step.

From 1 kg of biomass, 340±100 mg of purified IFNα2c were obtained. The yield of the purification process is 56.1±22.2%. The total yield, based on the IFNα2c content of the biomass, is 14.4%. These data are shown in Table 7. FIG. 4 shows a typical SDS-PAGE of purified IFNα2c, eluting in the last chromatographic step. The 18 kDa band of IFNα2c is the only visible band. No contaminating bands are observed. FIG. 5A shows a typical reversed phase HPLC chromatogram. The purified IFNα2c elutes as a homogeneous peak at 24.8 minutes. When this material was eluted with a flat acetonitrile gradient (FIG. 5B), 2 contamination peaks were observed on either side of the main peak. These shoulders, which contain approximately 1.8% of the total IFNα2c content, represent forms which are oxidized at the methionine 111 (first shoulder) or acetylated at the N-terminus (second shoulder).

TABLE 5

Yields of various purification steps in percent of IFNα2 obtained after the purification step in question, shown for 6 different purification procedures (p1–p6) of 6 different biomasses. The last two columns contain the mean (M) and the standard deviation (sd).

|  | p1 | p2 | p3 | p4 | p5 | p6 | M | sd |
|---|---|---|---|---|---|---|---|---|
| Extract | 37.9 | 24.0 | 34.3 | 30.7 | 29.1 | 20.0 | 29.3 | 5.9 |
| Silica adsorption | 62.0 | 95.8 | 88.2 | 99.5 | 74.1 | 81.0 | 83.4 | 12.8 |
| Phenyl Sepharose™ | 100.0 | 82.2 | 85.9 | 100.0 | 100.0 | 91.0 | 93.2 | 7.3 |
| Sulphopropyl ion exchange | 64.0 | 54.3 | 76.5 | 100.0 | 60.0 | 71.0 | 70.9 | 14.8 |
| DEAE ion exchange | 95.0 | 100.0 | 83.5 | 88.2 | 84.0 | 71.0 | 86.9 | 9.2 |

TABLE 6

IFNα2 content of different purification steps. The data are shown as in Table 1, as a percentage of the IFNα2 content, based on the total protein content obtained in this purification step.

|  | p1 | p2 | p3 | p4 | p5 | p6 | M | sd |
|---|---|---|---|---|---|---|---|---|
| Extract | 8.0 | 2.1 | 4.1 | 4.7 | 3.6 | 4.4 | 4.5 | 1.8 |
| Silica adsorption | 12.9 | 11.6 | 15.7 | 15.7 | 19.4 | 15.6 | 16.7 | 4.4 |
| Phenyl Sepharose™ | 76.6 | 43.3 | 62.9 | 62.9 | 80.0 | 93.5 | 71.2 | 15.5 |
| Sulphopropyl ion exchange | 98.5 | 87.3 | 100.0 | 100.0 | 100.0 | 100.0 | 97.6 | 4.6 |
| DEAE ion exchange | 100.0 | 100.0 | 100.0 | 100.0 | 100.0 | 100.0 | 100.0 | 0.0 |

TABLE 7

Total yields of the purification process. The IFNα2c content of the biomass is shown as g of IFNα2/kg of biomass. Processing and extraction are expressed as a percentage of the total content of IFNα2. The yield of purification is shown as a percentage of IFNα2c relative to the IFNα2 content of the extract. The total yield is expressed in mg IFNα2, obtained per kg of biomass, and as a percentage of purified IFNα2c, based on the IFNα2c content of the extract.

|  | p1 | p2 | p3 | p4 | p5 | p6 | M | sd |
|---|---|---|---|---|---|---|---|---|
| Biomass [g/kg] | 1.4 | 1.0 | 1.1 | 1.5 | 1.1 | 1.8 | 1.3 | 0.2 |
| Processing [%] | 50 | 40 | 40 | 40 | 20 | 40 | 38.3 | 8.9 |
| Extraction [%] | 37.9 | 24.0 | 34.3 | 30.7 | 29.1 | 20.0 | 29.3 | 4.7 |
| Purification [%] | 39.7 | 42.7 | 57.9 | 90 | 44.5 | 52.3 | 56.1 | 22.2 |
| Total yield [mg] | 538 | 206 | 366 | 480 | 280 | 258 | 340 | 120 |
| Total yield [%] | 14.3 | 20.3 | 16.6 | 23.9 | 10.9 | 7.4 | 14.4 | 6.9 |

What is claimed is:

1. A method for preparing correctly folded and disulfide bond-linked interferon-α by expression in *E. coli*, comprising the steps of:
   (a) expressing interferon-α in *E. coli* transformed with a vector comprising an *E. coli* alkaline phosphatase (phoA) promoter operably linked to a nucleotide sequence encoding the signal peptide for the heat stable enterotoxin II (STII) of *E. coli*, said nucleotide sequence encoding the signal peptide being operably linked to a nucleotide sequence which codes for mature interferon-α; and
   (b) isolating the expressed interferon-α.

2. The method of claim 1 wherein said vector further comprises the sequence for the ribosome binding site of the STII gene.

3. The method of claim 1 wherein said isolating step comprises the steps of:
   (a) performing chromatography on silica gel;
   (b) performing hydrophobic interaction chromatography;
   (c) performing cation exchange chromatography; and
   (d) performing anion exchange chromatography.

4. The method of claim 3, wherein said hydrophobic interaction chromatography employs phenyl Sepharose™.

5. The method of claim 3, wherein said cation exchange chromatography employs a sulphopropyl ion exchanger.

6. The method of claim 3, wherein said anion exchange chromatography employs DEAE-Sepharose™.

7. The method of claim 1, wherein said interferon-α is interferon-α2.

8. The method of claim 7, wherein said interferon-α2 comprises the sequence:

Cys Asp Leu Pro Gln Thr His Ser Leu Gly Ser Arg Arg Thr

Leu Met Leu Leu Ala Gln Met Arg Arg Ile Ser Leu Phe Ser

Cys Leu Lys Asp Arg Arg Asp Phe Gly Phe Pro Gln Glu Glu

Phe Gly Asn Gln Phe Gln Lys Ala Glu Thr Ile Pro Val Leu

His Glu Met Ile Gln Gln Ile Phe Asn Leu Phe Ser Thr Lys

Asp Ser Ser Ala Ala Trp Asp Glu Thr Leu Leu Asp Lys Phe

Tyr Thr Glu Leu Tyr Gln Gln Leu Asn Asp Leu Glu Ala Cys

Val Ile Gln Gly Val Gly Val Thr Glu Thr Pro Leu Met Lys

Glu Asp Ser Ile Leu Ala Val Arg Lys Tyr Phe Gln Arg Ile

Thr Leu Tyr Leu Lys Glu Lys Lys Tyr Ser Pro Cys Ala Trp

Glu Val Val Arg Ala Glu Ile Met Arg Ser Phe Ser Leu Ser

Thr Asn Leu Gln Glu Ser Leu Arg Ser Lys Glu (SEQ ID NO: 5).

9. The method of claim 7, wherein said interferon-α2 is encoded by a nucleotide sequence comprising the sequence of SEQ ID NO:6 or a sequence encoding interferon-α which has more than about 70% sequence identity with this sequence.

10. The method of claim 7, wherein said interferon-α2 is encoded by a nucleotide sequence comprising the sequence of SEQ ID NO:7 or a sequence encoding interferon-α which has more than about 70% sequence identity with this sequence.

11. The method of claim 1, wherein 340±100 mg of said interferon-α is obtained from 1 kg of *E. coli*.

12. A vector for expressing interferon-α in *E. coli*, comprising an *E. coli* alkaline phosphatase (phoA) promoter operably linked to a nucleotide sequence coding for the signal peptide of the heat stable enterotoxin II (STII) of *E. coli*, wherein said nucleotide sequence coding for the signal peptide is operably linked to a nucleotide sequence which codes for mature human interferon-α.

13. The vector of claim 12, wherein said vector further comprises a ribosome binding site of the STII gene.

14. The vector of claim 12, wherein said interferon-α is interferon-α2.

15. The vector of claim 12, wherein said nucleotide sequence which codes for interferon-α comprises the sequence:

```
TGT GAT CTG CCT CAA ACC CAC AGC CTG GGT AGC AGG AGG ACC

TTG ATG CTC CTG GCA CAG ATG AGG AGA ATC TCT CTT TTC TCC

TGC TTG AAG GAC AGA CGT GAC TTT GGA TTT CCC CAG GAG GAG

TTT GGC AAC CAG TTC CAA AAG GCT GAA ACC ATC CCT GTC CTC

CAT GAG ATG ATC CAG CAG ATC TTC AAT CTC TTC AGC ACA AAG

GAC TCA TCT GCT GCT TGG GAT GAG ACC CTC CTA GAC AAA TTC

TAC ACT GAA CTC TAC CAG CAG CTG AAT GAC CTG GAA GCC TGT

GTG ATA CAG GGG GTG GGG GTG ACA GAG ACT CCC CTG ATG AAG

GAG GAC TCC ATT CTG GCT GTG AGG AAA TAC TTC CAA AGA ATC

ACT CTC TAT CTG AAA GAG AAG AAA TAC AGC CCT TGT GCC TGG

GAG GTT GTC AGA GCA GAA ATC ATG AGA TCT TTT TCT TTG TCA

ACA AAC TTG CAA GAA AGT TTA AGA AGT AAG GAA     (SEQ ID NO: 6)
``` or a sequence encoding interferon-α which has more than about 70% sequence identity with this sequence.

16. The vector of claim 12, wherein said nucleotide sequence which codes for interferon-α comprises the sequence:

```
GAATTCGAGATTATCGTCACTGCAATGCTTCGCAATATGGCGCAAAATGACCAACAG

CGGTTGATTGATCAGGTAGAGGGGGCGCTGTACGAGGTAAAGCCCGATGCCAGCATT

CCTGACGACGATACGGAGCTGCTGCGCGATTACGTAAAGAAGTTATTGAAGCATCCT

CGTCAGTAAAAAGTTAATCTTTTCAACAGCTGTCATAAAGTTGTCACGGCCGAGACT

TATAGTCGCTTTGTTTTTATTTTTTAATGTATTTGCTCGAGAGGTTGAGGTGATTTT

ATG AAA AAG AAT ATC GCA TTT CTT CTT GCA TCT ATG TTC GTT

TTT TCT ATT GCT ACA AAT CCC TAT GCA TGT GAT CTG CCT CAA

ACC CAC AGC CTG GGT AGC AGG AGG ACC TTG ATG CTC CTG GCA

CAG ATG AGG AGA ATC TCT CTT TTC TCC TGC TTG AAG GAC AGA

CGT GAC TTT GGA TTT CCC CAG GAG GAG TTT GGC AAC CAG TTC

CAA AAG GCT GAA ACC ATC CCT GTC CTC CAT GAG ATG ATC CAG

CAG ATC TTC AAT CTC TTC AGC ACA AAG GAC TCA TCT GCT GCT

TGG GAT GAG ACC CTC CTA GAC AAA TTC TAC ACT GAA CTC TAC

CAG CAG CTG AAT GAC CTG GAA GCC TGT GTG ATA CAG GGG GTG
```

-continued

```
GGG GTG ACA GAG ACT CCC CTG ATG AAG GAG GAC TCC ATT CTG

GCT GTG AGG AAA TAC TTC CAA AGA ATC ACT CTC TAT CTG AAA

GAG AAG AAA TAC AGC CCT TGT GCC TGG GAG GTT GTC AGA GCA

GAA ATC ATG AGA TCT TTT TCT TTG TCA ACA AAC TTG CAA GAA

AGT TTA AGA AGT AAG GAA TGATAACGATCGTAACTGCA  (SEQ ID NO:7)
``` or a sequence encoding interferon-α which has more than about 70% sequence identity with this sequence.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
    ( A ) LENGTH: 25 base pairs
    ( B ) TYPE: nucleic acid
    ( C ) STRANDEDNESS: both
    ( D ) TOPOLOGY: unknown ( i i ) MOLECULE TYPE: cDNA ( x i ) SEQUENCE DESCRIPTION: SEQ ID NO: 1:

CGTCTTCAAG AATTCGAGAT TATCG                       25

( 2 ) INFORMATION FOR SEQ ID NO: 2:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: unknown ( i i ) MOLECULE TYPE: cDNA ( x i ) SEQUENCE DESCRIPTION: SEQ ID NO: 2:

GACTTCAGAA GCTTCTGCAG TTACGATCGT TATCATTCCT TACTTCTTAA ACTTTC    56

( 2 ) INFORMATION FOR SEQ ID NO: 3:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: unknown ( i i ) MOLECULE TYPE: cDNA ( x i ) SEQUENCE DESCRIPTION: SEQ ID NO: 3:

ATGCCTATGC ATGTGATCTG CCTCAAACCC ACAGC                     35

( 2 ) INFORMATION FOR SEQ ID NO: 4:

( i ) SEQUENCE CHARACTERISTICS:
        ( A ) LENGTH: 34 base pairs
        ( B ) TYPE: nucleic acid
        ( C ) STRANDEDNESS: both
        ( D ) TOPOLOGY: unknown ( i i ) MOLECULE TYPE: cDNA ( x i ) SEQUENCE DESCRIPTION: SEQ ID NO: 4:

GGCAGATCAC ATGCATAGGC ATTTGTAGCA ATAG                      34

( 2 ) INFORMATION FOR SEQ ID NO: 5:

( i ) SEQUENCE CHARACTERISTICS:
        ( A ) LENGTH: 165 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

```
Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
             20                  25                  30

Arg Arg Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60
```

```
Asn  Leu  Phe  Ser  Thr  Lys  Asp  Ser  Ser  Ala  Ala  Trp  Asp  Glu  Thr  Leu
 65             70                       75                            80

Leu  Asp  Lys  Phe  Tyr  Thr  Glu  Leu  Tyr  Gln  Gln  Leu  Asn  Asp  Leu  Glu
                85                       90                            95

Ala  Cys  Val  Ile  Gln  Gly  Val  Gly  Val  Thr  Glu  Thr  Pro  Leu  Met  Lys
               100                      105                      110

Glu  Asp  Ser  Ile  Leu  Ala  Val  Arg  Lys  Tyr  Phe  Gln  Arg  Ile  Thr  Leu
          115                      120                      125

Tyr  Leu  Lys  Glu  Lys  Lys  Tyr  Ser  Pro  Cys  Ala  Trp  Glu  Val  Val  Arg
          130                 135                      140

Ala  Glu  Ile  Met  Arg  Ser  Phe  Ser  Leu  Ser  Thr  Asn  Leu  Gln  Glu  Ser
 145                     150                      155                     160

Leu  Arg  Ser  Lys  Glu
               165
```

( 2 ) INFORMATION FOR SEQ ID NO: 6:

( i ) SEQUENCE CHARACTERISTICS:
        ( A ) LENGTH: 495 base pairs
        ( B ) TYPE: nucleic acid
        ( C ) STRANDEDNESS: both
        ( D ) TOPOLOGY: unknown ( i i ) MOLECULE TYPE: cDNA ( i x ) FEATURE:
        ( A ) NAME/KEY: CDS
        ( B ) LOCATION: 1..495

( x i ) SEQUENCE DESCRIPTION: SEQ ID NO: 6:

```
TGT  GAT  CTG  CCT  CAA  ACC  CAC  AGC  CTG  GGT  AGC  AGG  AGG  ACC  TTG  ATG    48
Cys  Asp  Leu  Pro  Gln  Thr  His  Ser  Leu  Gly  Ser  Arg  Arg  Thr  Leu  Met
 1                   5                       10                       15

CTC  CTG  GCA  CAG  ATG  AGG  AGA  ATC  TCT  CTT  TTC  TCC  TGC  TTG  AAG  GAC    96
Leu  Leu  Ala  Gln  Met  Arg  Arg  Ile  Ser  Leu  Phe  Ser  Cys  Leu  Lys  Asp
                20                       25                       30

AGA  CGT  GAC  TTT  GGA  TTT  CCC  CAG  GAG  GAG  TTT  GGC  AAC  CAG  TTC  CAA   144
Arg  Arg  Asp  Phe  Gly  Phe  Pro  Gln  Glu  Glu  Phe  Gly  Asn  Gln  Phe  Gln
           35                       40                       45

AAG  GCT  GAA  ACC  ATC  CCT  GTC  CTC  CAT  GAG  ATG  ATC  CAG  CAG  ATC  TTC   192
Lys  Ala  Glu  Thr  Ile  Pro  Val  Leu  His  Glu  Met  Ile  Gln  Gln  Ile  Phe
      50                       55                       60

AAT  CTC  TTC  AGC  ACA  AAG  GAC  TCA  TCT  GCT  GCT  TGG  GAT  GAG  ACC  CTC   240
Asn  Leu  Phe  Ser  Thr  Lys  Asp  Ser  Ser  Ala  Ala  Trp  Asp  Glu  Thr  Leu
 65                  70                       75                       80

CTA  GAC  AAA  TTC  TAC  ACT  GAA  CTC  TAC  CAG  CAG  CTG  AAT  GAC  CTG  GAA   288
Leu  Asp  Lys  Phe  Tyr  Thr  Glu  Leu  Tyr  Gln  Gln  Leu  Asn  Asp  Leu  Glu
                85                       90                       95

GCC  TGT  GTG  ATA  CAG  GGG  GTG  GGG  GTG  ACA  GAG  ACT  CCC  CTG  ATG  AAG   336
Ala  Cys  Val  Ile  Gln  Gly  Val  Gly  Val  Thr  Glu  Thr  Pro  Leu  Met  Lys
               100                      105                      110

GAG  GAC  TCC  ATT  CTG  GCT  GTG  AGG  AAA  TAC  TTC  CAA  AGA  ATC  ACT  CTC   384
Glu  Asp  Ser  Ile  Leu  Ala  Val  Arg  Lys  Tyr  Phe  Gln  Arg  Ile  Thr  Leu
          115                      120                      125

TAT  CTG  AAA  GAG  AAG  AAA  TAC  AGC  CCT  TGT  GCC  TGG  GAG  GTT  GTC  AGA   432
Tyr  Leu  Lys  Glu  Lys  Lys  Tyr  Ser  Pro  Cys  Ala  Trp  Glu  Val  Val  Arg
          130                 135                      140

GCA  GAA  ATC  ATG  AGA  TCT  TTT  TCT  TTG  TCA  ACA  AAC  TTG  CAA  GAA  AGT   480
Ala  Glu  Ile  Met  Arg  Ser  Phe  Ser  Leu  Ser  Thr  Asn  Leu  Gln  Glu  Ser
 145                     150                      155                     160

TTA  AGA  AGT  AAG  GAA                                                           495
```

Leu Arg Ser Lys Glu
                165

(2) INFORMATION FOR SEQ ID NO: 7:

(i) SEQUENCE CHARACTERISTICS:
        (A) LENGTH: 869 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 7:

```
GAATTCGAGA TTATCGTCAC TGCAATGCTT CGCAATATGG CGCAAAATGA CCAACAGCGG   60
TTGATTGATC AGGTAGAGGG GGCGCTGTAC GAGGTAAAGC CCGATGCCAG CATTCCTGAC  120
GACGATACGG AGCTGCTGCG CGATTACGTA AAGAAGTTAT TGAAGCATCC TCGTCAGTAA  180
AAAGTTAATC TTTTCAACAG CTGTCATAAA GTTGTCACGG CCGAGACTTA TAGTCGCTTT  240
GTTTTTATTT TTAATGTAT  TTGCTCGAGA GGTTGAGGTG ATTTATGAA  AAGAATATC   300
GCATTTCTTC TTGCATCTAT GTTCGTTTTT TCTATTGCTA CAAATGCCTA TGCATGTGAT  360
CTGCCTCAAA CCCACAGCCT GGGTAGCAGG AGGACCTTGA TGCTCCTGGC ACAGATGAGG  420
AGAATCTCTC TTTTCTCCTG CTTGAAGGAC AGACGTGACT TTGGATTTCC CCAGGAGGAG  480
TTTGGCAACC AGTTCCAAAA GGCTGAAACC ATCCCTGTCC TCCATGAGAT GATCCAGCAG  540
ATCTTCAATC TCTTCAGCAC AAAGGACTCA TCTGCTGCTT GGGATGAGAC CCTCCTAGAC  600
AAATTCTACA CTGAACTCTA CCAGCAGCTG AATGACCTGG AAGCCTGTGT GATACAGGGG  660
GTGGGGGTGA CAGAGACTCC CCTGATGAAG GAGGACTCCA TTCTGGCTGT GAGGAAATAC  720
TTCCAAAGAA TCACTCTCTA TCTGAAAGAG AAGAAATACA GCCCTTGTGC CTGGGAGGTT  780
GTCAGAGCAG AAATCATGAG ATCTTTTTCT TTGTCAACAA ACTTGCAAGA AAGTTTAAGA  840
AGTAAGGAAT GATAACGATC GTAACTGCA                                    869
```

(2) INFORMATION FOR SEQ ID NO: 8:

(i) SEQUENCE CHARACTERISTICS:
        (A) LENGTH: 1177 base pairs
        (B) TYPE: nucleic acid
        (C) STRANDEDNESS: both
        (D) TOPOLOGY: unknown (ii) MOLECULE TYPE: cDNA (ix) FEATURE:
        (A) NAME/KEY: CDS
        (B) LOCATION: 286..873
        (D) OTHER INFORMATION: /function="Cytokine"
            / product="Interferon-omega1"

(ix) FEATURE:
        (A) NAME/KEY: mat_peptide
        (B) LOCATION: 355..873
        (D) OTHER INFORMATION: /function="Cytokine"
            / product="Interferon-omega"

(ix) FEATURE:
        (A) NAME/KEY: sig_peptide
        (B) LOCATION: 286..354
        (D) OTHER INFORMATION: /product="ST II Leader"

(xi) SEQUENCE DESCRIPTION: SEQ ID NO: 8:

```
GAATTGGAGA TTATCGTCAC TGCAATGCTT CGCAATATGG CGCAAAATGA CCAACAGCGG   60
TTGATTGATC AGGTAGAGGG GGCGCTGTAC GAGGTAAAGC CCGATGCCAG CATTCCTGAC  120
```

```
GACGATACGG AGCTGCTGCG CGATTACGTA AAGAAGTTAT TGAAGCATCC TCGTCAGTAA    180

AAAGTTAATC TTTTCAACAG CTGTCATAAA GTTGTCACGG CCGAGACTTA TAGTCGCTTT    240

GTTTTTATTT TTTAATGTAT TTGCTCGAGA GGTTGAGGTG ATTTT ATG AAA AAG        294
                                                  Met Lys Lys
                                                  -23

AAT ATC GCA TTT CTT CTT GCA TCT ATG TTC GTT TTT TCT ATT GCT ACA      342
Asn Ile Ala Phe Leu Leu Ala Ser Met Phe Val Phe Ser Ile Ala Thr
-20             -15                 -10                     -5

AAT GCC TAT GCA TGT GAT CTG CCT CAG AAC CAT GGC CTA CTT AGC AGG      390
Asn Ala Tyr Ala Cys Asp Leu Pro Gln Asn His Gly Leu Leu Ser Arg
                1               5                   10

AAC ACC TTG GTG CTT CTG CAC CAA ATG AGG AGA ATC TCC CCT TTC TTG      438
Asn Thr Leu Val Leu Leu His Gln Met Arg Arg Ile Ser Pro Phe Leu
        15                  20                  25

TGT CTC AAG GAC AGA AGA GAC TTC AGG TTC CCC CAG GAG ATG GTA AAA      486
Cys Leu Lys Asp Arg Arg Asp Phe Arg Phe Pro Gln Glu Met Val Lys
        30              35                  40

GGG AGC CAG TTG CAG AAG GCC CAT GTC ATG TCT GTC CTC CAT GAG ATG      534
Gly Ser Gln Leu Gln Lys Ala His Val Met Ser Val Leu His Glu Met
45              50                  55                  60

CTG CAG CAG ATC TTC AGC CTC TTC CAC ACA GAG CGC TCC TCT GCT GCC      582
Leu Gln Gln Ile Phe Ser Leu Phe His Thr Glu Arg Ser Ser Ala Ala
                65              70                  75

TGG AAC ATG ACC CTC CTA GAC CAA CTC CAC ACT GGA CTT CAT CAG CAA      630
Trp Asn Met Thr Leu Leu Asp Gln Leu His Thr Gly Leu His Gln Gln
                80              85                  90

CTG CAA CAC CTG GAG ACC TGC TTG CTG CAG GTA GTG GGA GAA GGA GAA      678
Leu Gln His Leu Glu Thr Cys Leu Leu Gln Val Val Gly Glu Gly Glu
        95                  100                 105

TCT GCT GGG GCA ATT AGC AGC CCT GCA CTG ACC TTG AGG AGG TAC TTC      726
Ser Ala Gly Ala Ile Ser Ser Pro Ala Leu Thr Leu Arg Arg Tyr Phe
110             115                 120

CAG GGA ATC CGT GTC TAC CTG AAA GAG AAG AAA TAC AGC GAC TGT GCC      774
Gln Gly Ile Arg Val Tyr Leu Lys Glu Lys Lys Tyr Ser Asp Cys Ala
125             130                 135                 140

TGG GAA GTT GTC AGA ATG GAA ATC ATG AAA TCC TTG TTC TTA TCA ACA      822
Trp Glu Val Val Arg Met Glu Ile Met Lys Ser Leu Phe Leu Ser Thr
                145                 150                 155

AAC ATG CAA GAA AGA CTG AGA AGT AAA GAT AGA GAC CTG GGC TCA TCT      870
Asn Met Gln Glu Arg Leu Arg Ser Lys Asp Arg Asp Leu Gly Ser Ser
                160                 165                 170

TGAAATGATT CTCATTGATT AATTTGCCAT ATAACACTTG CACATGTGAC TCTGGTCAAT    930

TCAAAAGACT CTTATTTCGG CTTAATCAC AGAATTGACT GAATTAGTTC TGCAAATACT     990

TTGTCGGTAT ATTAAGCCAG TATATGTTAA AAAGACTTAG GTTCAGGGGC ATCAGTCCCT   1050

AAGATGTTAT TTATTTTTAC TCATTTATTT ATTCTTACAT TTTATCATAT TTATACTATT   1110

TATATTCTTA TATAACAAAT GTTTGCCTTT ACATTGTATT AAGATAACAA AACATGTTCA   1170

GGATCCA                                                              1177
```

( 2 ) INFORMATION FOR SEQ ID NO: 9:

( i ) SEQUENCE CHARACTERISTICS:
        ( A ) LENGTH: 195 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

| | | | | | | | | | | | | |
|---|---|---|---|---|---|---|---|---|---|---|---|---|
| Met<br>-23 | Lys | Lys | Asn<br>-20 | Ile | Ala | Phe | Leu | Leu<br>-15 | Ala | Ser | Met | Phe | Val<br>-10 | Phe | Ser |
| Ile | Ala | Thr<br>-5 | Asn | Ala | Tyr | Ala | Cys<br>1 | Asp | Leu | Pro | Gln<br>5 | Asn | His | Gly | Leu |
| Leu<br>10 | Ser | Arg | Asn | Thr | Leu<br>15 | Val | Leu | Leu | His | Gln<br>20 | Met | Arg | Arg | Ile | Ser<br>25 |
| Pro | Phe | Leu | Cys | Leu<br>30 | Lys | Asp | Arg | Arg | Asp<br>35 | Phe | Arg | Phe | Pro | Gln<br>40 | Glu |
| Met | Val | Lys | Gly<br>45 | Ser | Gln | Leu | Gln | Lys<br>50 | Ala | His | Val | Met | Ser<br>55 | Val | Leu |
| His | Glu | Met<br>60 | Leu | Gln | Gln | Ile | Phe<br>65 | Ser | Leu | Phe | His | Thr<br>70 | Glu | Arg | Ser |
| Ser | Ala | Ala<br>75 | Trp | Asn | Met | Thr | Leu<br>80 | Leu | Asp | Gln | Leu | His<br>85 | Thr | Gly | Leu |
| His<br>90 | Gln | Gln | Leu | Gln | His<br>95 | Leu | Glu | Thr | Cys | Leu<br>100 | Leu | Gln | Val | Val | Gly<br>105 |
| Glu | Gly | Glu | Ser | Ala<br>110 | Gly | Ala | Ile | Ser | Ser<br>115 | Pro | Ala | Leu | Thr | Leu<br>120 | Arg |
| Arg | Tyr | Phe | Gln<br>125 | Gly | Ile | Arg | Val | Tyr<br>130 | Leu | Lys | Glu | Lys | Lys<br>135 | Tyr | Ser |
| Asp | Cys | Ala<br>140 | Trp | Glu | Val | Val | Arg<br>145 | Met | Glu | Ile | Met | Lys<br>150 | Ser | Leu | Phe |
| Leu | Ser<br>155 | Thr | Asn | Met | Gln | Glu<br>160 | Arg | Leu | Arg | Ser | Lys<br>165 | Asp | Arg | Asp | Leu |
| Gly<br>170 | Ser | Ser | | | | | | | | | | | | | |

( 2 ) INFORMATION FOR SEQ ID NO: 10:

( i ) SEQUENCE CHARACTERISTICS:
        ( A ) LENGTH: 879 base pairs
        ( B ) TYPE: nucleic acid
        ( C ) STRANDEDNESS: both
        ( D ) TOPOLOGY: unknown ( i i ) MOLECULE TYPE: cDNA ( i x ) FEATURE:
        ( A ) NAME/KEY: CDS
        ( B ) LOCATION: 286..852

( i x ) FEATURE:
        ( A ) NAME/KEY: mat_peptide
        ( B ) LOCATION: 355..852
        ( D ) OTHER INFORMATION: /function="Cytokine"
            / product="Interferon-alpha-2c"

( i x ) FEATURE:
        ( A ) NAME/KEY: sig_peptide
        ( B ) LOCATION: 286..354
        ( D ) OTHER INFORMATION: /product="ST II Leader"

( x i ) SEQUENCE DESCRIPTION: SEQ ID NO: 10:

```
GAATTCGAGA TTATCGTCAC TGCAATGCTT CGCAATATGG CGCAAAATGA CCAACAGCGG   60

TTGATTGATC AGGTAGAGGG GGCGCTGTAC GAGGTAAAGC CCGATGCCAG CATTCCTGAC  120

GACGATACGG AGCTGCTGCG CGATTACGTA AAGAAGTTAT GAAGCATCC TCGTCAGTAA   180

AAAGTTAATC TTTTCAACAG CTGTCATAAA GTTGTCACGG CCGAGACTTA TAGTCGCTTT  240

GTTTTTATTT TTAATGTAT TTGCTCGAGA GGTTGAGGTG ATTTT ATG AAA AAG        294
                                                  Met Lys Lys
                                                  -23

AAT ATC GCA TTT CTT CTT GCA TCT ATG TTC GTT TTT TCT ATT GCT ACA    342
```

```
Asn Ile Ala Phe Leu Leu Ala Ser Met Phe Val Phe Ser Ile Ala Thr
-20              -15                     -10                        -5

AAT GCC TAT GCA TGT GAT CTG CCT CAA ACC CAC AGC CTG GGT AGC AGG     390
Asn Ala Tyr Ala Cys Asp Leu Pro Gln Thr His Ser Leu Gly Ser Arg
                 1               5                       10

AGG ACC TTG ATG CTC CTG GCA CAG ATG AGG AGA ATC TCT CTT TTC TCC     438
Arg Thr Leu Met Leu Leu Ala Gln Met Arg Arg Ile Ser Leu Phe Ser
         15              20                  25

TGC TTG AAG GAC AGA CGT GAC TTT GGA TTT CCC CAG GAG GAG TTT GGC     486
Cys Leu Lys Asp Arg Arg Asp Phe Gly Phe Pro Gln Glu Glu Phe Gly
         30              35                  40

AAC CAG TTC CAA AAG GCT GAA ACC ATC CCT GTC CTC CAT GAG ATG ATC     534
Asn Gln Phe Gln Lys Ala Glu Thr Ile Pro Val Leu His Glu Met Ile
45               50              55                       60

CAG CAG ATC TTC AAT CTC TTC AGC ACA AAG GAC TCA TCT GCT GCT TGG     582
Gln Gln Ile Phe Asn Leu Phe Ser Thr Lys Asp Ser Ser Ala Ala Trp
                 65              70                       75

GAT GAG ACC CTC CTA GAC AAA TTC TAC ACT GAA CTC TAC CAG CAG CTG     630
Asp Glu Thr Leu Leu Asp Lys Phe Tyr Thr Glu Leu Tyr Gln Gln Leu
         80              85                  90

AAT GAC CTG GAA GCC TGT GTG ATA CAG GGG GTG GGG GTG ACA GAG ACT     678
Asn Asp Leu Glu Ala Cys Val Ile Gln Gly Val Gly Val Thr Glu Thr
         95              100                 105

CCC CTG ATG AAG GAG GAC TCC ATT CTG GCT GTG AGG AAA TAC TTC CAA     726
Pro Leu Met Lys Glu Asp Ser Ile Leu Ala Val Arg Lys Tyr Phe Gln
    110              115                 120

AGA ATC ACT CTC TAT CTG AAA GAG AAG AAA TAC AGC CCT TGT GCC TGG     774
Arg Ile Thr Leu Tyr Leu Lys Glu Lys Lys Tyr Ser Pro Cys Ala Trp
125              130             135                      140

GAG GTT GTC AGA GCA GAA ATC ATG AGA TCT TTT TCT TTG TCA ACA AAC     822
Glu Val Val Arg Ala Glu Ile Met Arg Ser Phe Ser Leu Ser Thr Asn
                 145             150                 155

TTG CAA GAA AGT TTA AGA AGT AAG GAA TGATAACGAT CGTAACTGCA           869
Leu Gln Glu Ser Leu Arg Ser Lys Glu
             160             165

GAAGCTTAAT                                                          879
```

( 2 ) INFORMATION FOR SEQ ID NO: 11:

( i ) SEQUENCE CHARACTERISTICS:
        ( A ) LENGTH: 188 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 11:

```
Met Lys Lys Asn Ile Ala Phe Leu Leu Ala Ser Met Phe Val Phe Ser
-23          -20              -15                     -10

Ile Ala Thr Asn Ala Tyr Ala Cys Asp Leu Pro Gln Thr His Ser Leu
         -5              1               5

Gly Ser Arg Arg Thr Leu Met Leu Leu Ala Gln Met Arg Arg Ile Ser
10                  15              20                  25

Leu Phe Ser Cys Leu Lys Asp Arg Arg Asp Phe Gly Phe Pro Gln Glu
             30              35                  40

Glu Phe Gly Asn Gln Phe Gln Lys Ala Glu Thr Ile Pro Val Leu His
             45              50                  55

Glu Met Ile Gln Gln Ile Phe Asn Leu Phe Ser Thr Lys Asp Ser Ser
             60              65                  70

Ala Ala Trp Asp Glu Thr Leu Leu Asp Lys Phe Tyr Thr Glu Leu Tyr
```

```
                      75                      80                          85
    Gln  Gln  Leu  Asn  Asp  Leu  Glu  Ala  Cys  Val  Ile  Gln  Gly  Val  Gly  Val
         90                       95                  100                      105

Thr  Glu  Thr  Pro  Leu  Met  Lys  Glu  Asp  Ser  Ile  Leu  Ala  Val  Arg  Lys
                       110                      115                      120

Tyr  Phe  Gln  Arg  Ile  Thr  Leu  Tyr  Leu  Lys  Glu  Lys  Lys  Tyr  Ser  Pro
                   125                      130                      135

Cys  Ala  Trp  Glu  Val  Val  Arg  Ala  Glu  Ile  Met  Arg  Ser  Phe  Ser  Leu
                   140                 145                      150

Ser  Thr  Asn  Leu  Gln  Glu  Ser  Leu  Arg  Ser  Lys  Glu
         155                      160                      165
```